(12) United States Patent
Crawford et al.

(10) Patent No.: US 11,965,853 B2
(45) Date of Patent: Apr. 23, 2024

(54) ELECTROCHEMICAL SENSORS

(71) Applicant: SCHLUMBERGER TECHNOLOGY CORPORATION, Sugar Land, TX (US)

(72) Inventors: Lynne Crawford, Harlow (GB); Andrew Meredith, Cambridge (GB); Nathan Lawrence, Wyton (GB); Timothy Jones, Cottenham (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 309 days.

(21) Appl. No.: 14/365,624

(22) PCT Filed: Dec. 21, 2012

(86) PCT No.: PCT/IB2012/057638
§ 371 (c)(1),
(2) Date: Jun. 14, 2014

(87) PCT Pub. No.: WO2013/093888
PCT Pub. Date: Jun. 27, 2013

(65) Prior Publication Data
US 2014/0367277 A1    Dec. 18, 2014

(30) Foreign Application Priority Data

Dec. 23, 2011 (GB) ..................................... 1122301

(51) Int. Cl.
*G01N 27/28* (2006.01)
*E21B 47/00* (2012.01)
(Continued)

(52) U.S. Cl.
CPC ............ *G01N 27/28* (2013.01); *E21B 47/00* (2013.01); *G01N 27/302* (2013.01);
(Continued)

(58) Field of Classification Search
None
See application file for complete search history.

(56) References Cited

U.S. PATENT DOCUMENTS

| 3,780,575 A | 12/1973 | Urbanosky |
| 3,859,851 A | 1/1975 | Urbanosky |

(Continued)

FOREIGN PATENT DOCUMENTS

| CN | 101870467 A | 10/2010 |
| GB | 2409902 B | 4/2006 |

(Continued)

OTHER PUBLICATIONS

Lopez et al. A new multifunctional ferrocenyl-substituted ferrocenophane derivative: optical and electronic properties and selective recognition of Mg2+ ions. Chem. Eur. J. (2004); 10, p. 1815-1826.*

(Continued)

*Primary Examiner* — Benjamin R Whatley
(74) *Attorney, Agent, or Firm* — Jeffrey D. Frantz

(57) ABSTRACT

An electrochemical sensor incorporates a ferrocenophane which is a compound with at least one bridging group covalently attached to and connecting the two cyclopentadiene rings associated with the same iron atom. This bridging group maybe tetramethylene. As compared to an equivalent sensor with ferrocene, the tolerance of elevated temperature is improved and so is the working life at ambient temperature.

18 Claims, 6 Drawing Sheets

(51) Int. Cl.
 *G01N 27/30* (2006.01)
 *G01N 27/48* (2006.01)
 *G01N 33/18* (2006.01)

(52) U.S. Cl.
 CPC ........... *G01N 27/308* (2013.01); *G01N 27/48* (2013.01); *G01N 33/1886* (2013.01)

(56) References Cited

U.S. PATENT DOCUMENTS

| | | | |
|---|---|---|---|
| 4,648,478 | A | 3/1987 | Dedole |
| 4,702,343 | A | 10/1987 | Paulsson |
| 4,711,245 | A | 12/1987 | Higgins et al. |
| 4,932,003 | A | 6/1990 | Winbow |
| 4,994,671 | A | 2/1991 | Safinya et al. |
| 5,115,880 | A | 5/1992 | Sallas et al. |
| 5,159,160 | A | 10/1992 | Brett |
| 5,223,117 | A | 6/1993 | Wrighton |
| 5,229,554 | A | 7/1993 | Cole |
| 5,309,405 | A | 5/1994 | Brett |
| 5,893,383 | A | 4/1999 | Facteau |
| 6,015,010 | A | 1/2000 | Kostrov |
| 6,059,031 | A | 5/2000 | Brett |
| 6,179,084 | B1 | 1/2001 | Yamamoto |
| 6,247,533 | B1 | 6/2001 | Brett |
| 6,321,836 | B2 | 11/2001 | Brett |
| 6,550,534 | B2 | 4/2003 | Brett |
| 6,905,667 | B1 | 6/2005 | Chen |
| 6,939,717 | B2 | 9/2005 | Jiang et al. |
| 7,125,533 | B2 | 10/2006 | Khabashesku |
| 7,182,170 | B1 | 2/2007 | Brett |
| 7,758,734 | B2 | 7/2010 | Jiang et al. |
| 9,791,399 | B2 | 10/2017 | McGuinness |
| 2004/0222081 | A1 | 11/2004 | Tour |
| 2005/0147553 | A1 | 7/2005 | Wong |
| 2006/0243603 | A1 | 11/2006 | Jiang et al. |
| 2007/0059732 | A1* | 3/2007 | Bamdad ............... B01J 13/00 435/6.11 |
| 2007/0272552 | A1* | 11/2007 | Jiang .................. E21B 47/10 204/422 |
| 2007/0280876 | A1 | 12/2007 | Tour |
| 2008/0023328 | A1 | 1/2008 | Jiang et al. |
| 2009/0178921 | A1* | 7/2009 | Lawrence ............ E21B 47/01 204/400 |
| 2009/0218239 | A1* | 9/2009 | Gooding ............ G01N 33/542 205/792 |
| 2009/0301896 | A1 | 12/2009 | Tour |
| 2010/0009432 | A1 | 1/2010 | Lee |
| 2010/0050761 | A1 | 3/2010 | Lawrence |
| 2010/0148780 | A1 | 6/2010 | Lawrence |
| 2010/0243480 | A1* | 9/2010 | Jiang .................. E21B 47/00 205/786.5 |
| 2010/0270178 | A1 | 10/2010 | Guo et al. |
| 2011/0048969 | A1 | 3/2011 | Lawrence et al. |
| 2011/0094732 | A1 | 4/2011 | Lehman et al. |
| 2011/0162977 | A1* | 7/2011 | Lafitte ................ G01N 27/48 205/775 |
| 2011/0317253 | A1* | 12/2011 | Han .................... C08G 77/58 359/321 |
| 2012/0059198 | A1* | 3/2012 | Zou ..................... B82Y 30/00 568/930 |
| 2012/0067745 | A1* | 3/2012 | Duimstra ............ G01N 27/36 205/789 |
| 2014/0332413 | A1 | 11/2014 | Crawford et al. |
| 2014/0353175 | A1 | 12/2014 | Crawford et al. |

FOREIGN PATENT DOCUMENTS

| | | | | |
|---|---|---|---|---|
| GB | 2430749 | B | 11/2007 | |
| GB | 2461555 | A | 1/2010 | |
| GB | 2468714 | A | 9/2010 | |
| WO | 0140623 | A1 | 6/2001 | |
| WO | 0163094 | A1 | 8/2001 | |
| WO | 2004011929 | A1 | 2/2004 | |
| WO | 2004063743 | A1 | 7/2004 | |
| WO | 2005028174 | A2 | 3/2005 | |
| WO | 2005066618 | A1 | 7/2005 | |
| WO | 2007034131 | A1 | 3/2007 | |
| WO | 2007100352 | A1 | 9/2007 | |
| WO | 2009093081 | A1 | 7/2009 | |
| WO | 2010001082 | A1 | 1/2010 | |
| WO | WO-2010104962 | A1 * | 9/2010 | ............ G01N 27/36 |
| WO | WO 2010106404 | A2 * | 9/2010 | ............ B82Y 30/00 |
| WO | 2013090488 | A1 | 6/2013 | |

OTHER PUBLICATIONS

Issa et al. Potentiometric measurement of state-of-charge of lead-acid battery by using a bridged ferrocene surface modified electrode. Journal of Power Sources. (2006); 158, p. 1034-1038.*

Clara et al. Femtosecond laser mass spectroscopy of ferrocenes: photochemical stabilization by bridged cyclopentadienyl rings. International Journal of Mass Spectrometry. (2000); 203, p. 71-81.*

Cui et al. Rigid ferrocenophane and its metal complexes with transition and alkaline-earth metal ions. Polyhedron. (2010); 29, p. 1697-1705.*

Lawrence et al. Ferrocene sulfonates as electrocatalysts for sulfide detection; Electrochimica Acta; 52, (2006), p. 499-503.*

Heo et al (Ferrocenophanes with all carbon bridges; Journal of Organometallic Chemistry; 578 (1999), pp. 31-42).*

Banks, et al., "Exploring Alkylated Ferrocene Sulfonates as Electrocatalysts for Sulfide Detection", Electroanalysis, vol. 19, Issue 24, Dec. 2007, pp. 2518-2522.

Bohn, et al., "On the molecular structure of ferrocene, Fe(C5H5)2", Journal of Organometallic Chemistry, vol. 5, Issue 5, May 1966, pp. 470-476.

Cui, et al., "Rigid ferrocenophane and its metal complexes with transition and alkaline-earth metal ions", Polyhedron, vol. 29, Issue 6, Apr. 19, 2010, pp. 1697-1705.

Dunitz, et al., "The crystal structure of ferrocene", Acta Crystallographica, vol. 9, Issue 4, Apr. 1956, pp. 373-375.

Heo, et al., "Ferrocenophanes with all carbon bridges", Journal of Organometallic Chemistry, vol. 578, Issues 1-2, Apr. 22, 1999, pp. 31-42.

Hisatome, et al., "Organometallic compounds ☆: XXI. Syntheses of [4](1,1')[4](3,3')ferrocenophane and related compounds", Journal of Organometallic Chemistry, vol. 107, Issue 1, Feb. 24, 1976, pp. 87-101.

Issa, et al., "Potentiometric measurement of state-of-charge of lead-acid battery by using a bridged ferrocene surface modified electrode", Journal of Power Sources, vol. 158, Issue 2, Aug. 25, 2006, pp. 1034-1038.

Lawrence, et al., "Amperometric Detection of Sulfide: An Electrocatalytic Reaction with Ferrocene Carboxylate", Electroanalysis, vol. 18, Issue 17, Sep. 2006, pp. 1658-1663.

Lawrence, et al., "Ferrocene sulfonates as electrocatalysts for sulfide detection", Electrochimica Acta, vol. 52, Issue 2, Oct. 25, 2006, pp. 499-503.

Lopez, et al., "A new multifunctional ferrocenyl-substituted ferrocenophane derivative: optical and electronic properties and selective recognition of Mg2+ ions", Chemistry, vol. 10, No. 7, Apr. 2, 2004, pp. 1815-1826.

Rosenblum, et al., "The Structure and Chemistry of Ferrocene", VII. Bridged Ferrocenes, Journal of the American Chemical Society, vol. 85, No. 3, 1963, pp. 316-324.

Scholz, et al., "Voltammetry of Solid Microparticles Immobilized on Electrode Surfaces", Electroanalytical Chemistry, A Series of Advances, vol. 20, Marcel Dekker, Inc.: New York, 1998, pp. 1-86.

Seibold, et al., "Structure of Ferrocene", The Journal of Chemical Physics, vol. 23, 1955, p. 1967.

Sola, et al., "Unprecedented 1,3-Diaza[3]ferrocenophane Scaffold as Molecular Probe for Anions", Inorganic Chemistry, vol. 50, No. 9, 2011, pp. 4212-4220.

Tustin, et al., "Synthesis and characterisation of water soluble ferrocenes: Molecular tuning of redox potentials", Journal of Organometallic Chemistry, vol. 692, Issue 23, Nov. 1, 2007, pp. 5173-5182.

(56) References Cited

OTHER PUBLICATIONS

Search Report issued in EP12858863.9 dated Apr. 8, 2015, 5 pages.
Examination Report issued in GB1122301.3 dated Apr. 22, 2015, 3 pages.
Extended Search Report issued in EP12858863.9 dated May 6, 2015, 5 pages.
International Search Report and Written Opinion for corresponding PCT Application Serial No. PCT/IB2012/057638, dated May 15, 2013, 12 pages.
Examination Report issued in GB1122301.3 dated Apr. 17, 2012, 3 pages.
Barr, et al, "Bridged Ferrocenes—V Seric and Conformational Effects in the Acetylation of [m]Ferrocenophanes", Tetrahedron, vol. 25, pp. 5245-5253, (1969).
Chen et al., "Redox-active Conducting Polymers Incorporating Ferrocenes 2. Prepreparation and Characterisation of Polypyrroles Containing Propyl-andbutyl-tethered [1.1] ferrocenophane," Electrochimica Acta, vol. 49, (2004), pp. 691-702.
Deinhammer et al., "Electrochemical Oxidation of Amine-Containing Compounds: A Route to the Surface Modification of Glassy Carbon Electrodes," Lanmuir (1994) vol. 10, pp. 1306-1313.
Guo, et al., "Modification of a Glassy Carbon Electrode with Diols for the Suppression of Electrode Fouling in Biological Fluids," Chem. Parm. Bull. vol. 44, No. 4, (1995) pp. 860-862.
Hayes, et al., "Preservation of NADH Voltammetry for Enzyme-Modified Electrodes Based on Dehydrogenase", Anal. Chem, (1999) vol. 71, pp. 1720-1727.
Hillman et al, "Bridged Ferrocenes 10. Structural Phenomena," Organometallics (1984) vol. 3, pp. 1170-1177.
Hisatome et al., "Organometallic Compounds XXIII Formation of Novel DI- and Tri-Bridged Ferrocenophanes," J. Organometallic Chem. vol. 125, (1977) pp. 79-93.
Holzinger et al, "Sidewall Functionalization of Carbon Nanotubes", Angew. Chem., Int. Ed (2001), vol. 40, No. 21, pp. 4002-4005.
Mueller-Westerhoff, "[m]Metallocenophanes: Synthesis, Structure, and Properties," Angew. Chem., Int. Ed. Engl. (1986), vol. 25, pp. 702-717.
Oton et al, "Selective Metal-Cation Recognition by [2.2]Ferrocenophanes: The Cases of Zinc- and Lithium-Sensing," Chem. Eur. J. (2010) vol. 16, 1532-1542.
Watts, "The Friedel—Crafts Route to the [1.1] Ferrocenophane System," J. Organomeial Chem. vol. 10 (1967) 191-192.
European Examination Report for corresponding European Application Serial No. 12858863.9, dated Apr. 40, 2018, 5 pages.
International Preliminary Report on Patentability issued in International Patent Application No. PCT/IB2012/057638, dated Jun. 24, 2014, 6 pages.
Luttringhaus et al, Ansa-Ferrocene, Angewandte Chemie, vol. 58, Jun. 9, 1958, p. 438.
Delamar et al., "Covalent Modification of Carbon Surfaces by Grafting of Functionalized Aryl Radicals Produced from Electrochemical Reduction of Diazonium Salts," J. Am. Chem. Soc. vol. 114, pp. 5883-5884 (1992).
Mihai, et al., "Poly(ferrocenylenevinylene) from Ring-Opening Metathesis Polymerization of ansa-(Vinylene) ferrocene", Organometallics, vol. 16, No. 7, 1997, pp. 1507-1510.
Perng, et al., "Studies on the mesomorphic properties of ferrocenylene-based organophosphorous liquid-crystalline polymers containing phenyl and biphenyl pendant units", Journal of Applied Polymer Science, vol. 85, Issue 4, Jul. 25, 2002, pp. 831-841.
Wong, et al., "Covalently functionalized nanotubes as nanometre-sized probes in chemistry and biology", Nature, vol. 394, Jul. 2, 1998, pp. 52-55.
Tasis, et al., "Chemistry of Carbon Nanotubes", Chem. Rev., vol. 106, 2006, pp. 1105-1136.
Hirsch, et al., "Chapter 1. Functionalization of Carbon Nanotubes", Functional Organic Materials: Syntheses, Strategies and Applications, Wiley-VCH Verlag GmbH & Co. KGaA, Weinheim, Germany, Jan. 16, 2007.
Peng, et al., "Functional Covalent Chemistry of Carbon Nanotube Surfaces", Advanced Materials, vol. 21, Issue 6, Feb. 9, 2009, pp. 625-642.
Singh, et al., "Organic functionalisation and characterisation of single-walled carbon nanotubes", Chem. Soc. Rev., vol. 38, 2009, pp. 2214-2230.
Hauke, et al., "Chapter 6: Covalent Functionalization of Carbon Nanotubes", Carbon Nanotubes and related Structures—Synthesis, Characterization, Functionalization, and Applications, 2010, pp. 135-198.
Graupner, et al., "Chapter 16: Functionalization of Single-Walled Carbon Nanotubes: Chemistry and Characterization", Oxford Handbook of Nanoscience and Technology, vol. 1, 2010, p. 508.
Graupner, et al., "Nucleophilic-Alkylation-Reoxidation: A Functionalization Sequence for Single-Wall Carbon Nanotubes", Journal of the American Chemical Society, vol. 128, Issue 20, May 2, 2006, pp. 6683-6689.
Syrgiannis, et al., "Covalent Sidewall Functionalization of SWNTs by Nucleophilic Addition of Lithium Amides", European Journal of Organic Chemistry, vol. 2008, Issue 15, May 2008, pp. 2544-2550.
Gebhardt, et al., "A Novel Diameter-Selective Functionalization of SWCNTs with Lithium Alkynylides", European Journal of Organic Chemistry, vol. 2010, Issue 8, Jan. 29, 2010, pp. 1494-1501.
Wunderlich, et al., "Preferred Functionalization of Metallic and Small-Diameter Single-Walled Carbon Nanotubes by Nucleophilic Addition of Organolithium and -Magnesium Compounds Followed by Reoxidation", Chemistry—A European Journal, vol. 14, Issue 5, Feb. 8, 2008, pp. 1607-1614.
Campidelli, et al., "Functionalization of Carbon Nanotubes for Nanoelectronic and Photovoltaic Applications", John Wiley & Sons, Ltd., Chichester, West Sussex, United Kingdom, 2010, pp. 33-364.
Kanungo, et al., "Suppression of Metallic Conductivity of Single-Walled Carbon Nanotubes by Cycloaddition Reactions", Science, vol. 323, No. 5911, Jan. 2009, pp. 234-237.
International Search Report and Written Opinion issued in PCT Application PCT/IB2012/057617, dated Jun. 3, 2013 (11 pages).
International Preliminary Report on Patentability issued in PCT Application PCT/IB2012/057617, dated Jul. 3, 2014 (8 pages).
Search Report issued in GB Application 1122043.1 dated Sep. 14, 2012 (4 pages).
Akbar, et al., "Synthesis of polyethylene-grafted multiwalled carbon nanotubes via a peroxide-initiating radical coupling reaction and by using well-defined TEMP and thiol end-functionalized polyethylenes", Journal of Polymer Science: Part A Polymer Chemistry, vol. 49, 2011, pp. 957-965.
Examination Report issued in GB Application 1122043.1 dated Nov. 1, 2019 (12 pages).
Zanella, et al., "Deposition of Gold Nanoparticles onto Thiol-Functionalized Multiwalled Carbon Nanotubes", Journal of Physical Chemistry B., vol. 109, No. 34, 2005, pp. 16290-16295.
Examination Report issued in GB Application 1122043.1 dated May 22, 2020 (2 pages).
Temel et al., Modification of Multiwall carbon nanotube by thiol-ene click chemistry, Polym. Bull. (2013), 71: 3563-3574.
Zabini et al., One-pot synthesis of aminated multi-walled carbon nanotube using thiol-ene click chemistry for improvement of epoxy nanocomposites properties, RCS Adv, 2015 (8 pages).
Seibold, et al., "Structure of Ferrocene", Physical Chemistry Laboratory, Oxford University, Aug. 11, 1955, pp. 1967-1968.
Wildgoose, et al., "Graphite powder derivatised with poly-L-cysteine using "building-block" chemistry—a novel material for the extraction of heavy metal ions," J. Mater. Chem., No. 15, 2005, pp. 2375-2382.
Wildgoose, et al., "Chemically Modified Carbon Nanotubes for Use in Electroanalysis", Microchim. Acta, vol. 152, No. 3, 2006, pp. 187-214.
Zhou, et al., "Functionalized Single Wall Carbon Nanotubes Treated with Pyrrole for Electrochemical Supercapacitor Membranes", Chemistry of Materials, vol. 17, No. 8, 2005, pp. 1997-2002.

(56) References Cited

OTHER PUBLICATIONS

Liu, et al., "Preparing a Styrenic Polymer Composite Containing Well-Dispersed Carbon Nanotubes: Anionic Polymerization of a Nanotube-Bound p-Methylstyrene", Macromolecules, vol. 37, No. 2, 2004, pp. 283-287.
Viswanathan, et al., "Single-Step in Situ Synthesis of Polymer-Grafted Single-Wall Nanotube Composites", Journal of the American Chemical Society, vol. 125, No. 31, 2003, pp. 9258-9259.
Riggs, et al., "Optical Limiting Properties of Suspended and Solubilized Carbon Nanotubes", The Journal of Physical Chemistry B, vol. 104, No. 30, 2000, pp. 7071-7076.
Qin, et al., "Polymer Brushes on Single-Walled Carbon Nanotubes by Atom Transfer Radical Polymerization of n-Butyl Methacrylate", Journal of the American Chemical Society, vol. 126, No. 1, Dec. 10, 2003, pp. 170-176.
Kong, et al., "Controlled Functionalization of Multiwalled Carbon Nanotubes by in Situ Atom Transfer Radical Polymerization", Journal of the American Chemical Society, vol. 126, No. 2, Dec. 24, 2003, pp. 412-413.
Baker, et al., "Covalently Bonded Adducts of Deoxyribonucleic Acid (DNA) Oligonucleotides with Single-Wall Carbon Nanotubes: Synthesis and Hybridization", Nano Letters, vol. 2, No. 12, 2002, pp. 1413-1417.
McCarthy, et al., "Microscopy studies of nanotube-conjugated polymer interactions", Synthetic Metals, vol. 121, Mar. 15, 2001, pp. 1225-1226.
Fan, et al., "Synthesis, characterizations, and physical properties of carbon nanotubes coated by conducting polypyrrole", Journal of Applied Polymer Science, vol. 74, No. 11, Dec. 9, 1999, pp. 2605-2610.
Cochet, et al., "Synthesis of a new polyaniline/anotube composite: "in-situ" polymerisation and charge transfer through site-selective interaction", Chemical Communications, vol. 16, 2001, pp. 1450-1451.
O'Connell, et al., "Reversible water-solubilization of single-walled carbon nanotubes by polymer wrapping", Chemical Physics Letters, vol. 342, Issues 3-4, Jul. 13, 2001, pp. 265-271.
Barbier, et al., "Electrochemical Bonding of Amines to Carbon Fiber Surfaces Toward Improved Carbon-Epoxy Composites", Journal of The Electrochemical Society, vol. 137, Issue 6, 1990, pp. 1757-1764.
Antoniadou, et al., "Anion exchange activity of electrochemically bonded ethylene diamine on carbon fibres", Journal of Applied Electrochemistry, vol. 22, 1992, pp. 1060-1064.
Andrieux, et al., "Derivatization of Carbon Surfaces by Anodic Oxidation of Arylacetates: Electrochemical Manipulation of the Grafted Films", Journal of the American Chemical Society, vol. 119, No. 18, 1997, pp. 4292-4300.
Allongue, et al., "Covalent Modification of Carbon Surfaces by Aryl Radicals Generated from the Electrochemical Reduction of Diazonium Salts", Journal of the American Chemical Society, vol. 119, No. 1, 1997, pp. 201-207.
International Search Report and Written Opinion issued in PCT Application PCT/IB2012/057616, dated Jun. 10, 2013 (13 pages).
Leventis, et al., "Derivatised carbon powder electrodes: reagentless pH sensors", Talanta, vol. 63, No. 4, Jul. 8, 2004, pp. 1039-1051.
International Preliminary Report on Patentability issued in PCT Application PCT/IB2012/057616, dated Jun. 10, 2013 (13 pages).
Search Report issued in GB Application 1122058.9, dated Apr. 26, 2012 (6 pages).
Sadowska et al., Synthesis, charaterization and electrochemical testing of carbon nanotubes derivatized with azobenzene and anthraquinone, Carbon 47, 1501-1510, 2009.
Campidelli, et al., "Dendritic liquid-crystalline fullerene-ferrocene dyads", Tetrahedron, vol. 62, Issue 9, Supramolecular Chemistry of Fullerenes, Feb. 27, 2006, pp. 2115-2122.
Examination Report issued in GB Application 1122058.9, dated Aug. 16, 2019 (3 pages).

Bahr, et al., Functionalization of Carbon Nanotubes by Electrochemical Reduction of Aryl Diazonium Salts: A Bucky Paper Electrode, 2001, Journal of the American Chemical Society, vol. 123, pp. 6536-6542.
Švancara, et al., "Carbon Paste Electrodes in Modern Electroanalysis", Critical Reviews in Analytical Chemistry, vol. 31, Issue 4, 2001, p. 311.
Robinson, et al., "A Vinylanthracene and Vinylferrocene-Containing Copolymer: A New Dual pH/Sulfide Sensor", Wiley-VCH InterScience, Electroanalysis, (2006) pp. 678-683.
Robinson, et al., "Sulfide Sensing Via Differential Counter ion Diffusion rates Through Redox-Modulated Poly (Vinylferrocene) Microparticles", Electrochemistry Communications, vol. 8, (2006) pp. 1055-1061.
Robinson, et al., "Redox-Sensitive Copolymer: A Single-Component pH Sensor", Anal. Chem. (2006), vol. 78, pp. 2450-2455.
Moniruzzaman, et al., "Tuning the Mechanical Properties of SWNT/Nylon 6,10 Composites with Flexible Spacers at the Interface", American Chem. Soc., Nano Letters, vol. 7, (2007) pp. 1178-1185.
Holzinger, et al., "Sidewall Functionalization of Carbon Nanotubes", Angew. Chem. Int. Ed., vol. 40 (2001) pp. 4002-4005.
Lawrence, et al., "Selective Determination of Thiols: A Novel Electroanalytical Approach", Analyst, vol. 125, vol. 125, pp. 661-663.
Adams, et al., "Preparation and Characterization of Sulfonic Acid-Functionalized Single-Walled Carbon Nanotubes", Phisica E, vol. 41 (2009) pp. 723-728.
Jeroschewski, et al., "Galvanic Sensor for Determination of Hydrogen Sulfide", Electroanalysis, vol. 6 (1994) pp. 769-772.
Ye, et al., "Electrocatalytic O2 Reduction at Glassy Carbon Electrodes Modified with Dendrimer-Encapsulated Pt Nanoparticles", J. Am. Chem. Soc., vol. 127, pp. 4930-4934.
Delamar et al, "Modification of Carbon Fiber Surfaces by Electrochemical Reduction of Aryl Diazonium salts: Application to Carbon Epoxy Composites", Carbon vol. 35, pp. 801-807 (1997).
Ortiz et al., "Electrochemical Modification of a Carbon Electrode Using Aromatic Diazonium Salts. 2. Electrochemistry of 4-nitrophenyl Modified Glassy Carbon Electrodes in Aqueous Media," J. Electroanalytical Chemistry vol. 455 pp. 75-81 (1998).
Saby et al, "Electrochemical Modification of Glassy Carbon Electrode Using Aromatic Diazonium Salts. 1. Blocking Effect of 4-Nitrophenyl and 4-Carboxyphenyl Groups," Langmuir vol. 13, pp. 6805-6813 (1997).
Kroto, et al., "C60: Buckminsterfullerene", Nature, vol. 318, Nov. 14, 1985, pp. 162-163.
Iijima, et al., "Single-shell carbon nanotubes of 1-nm diameter", Nature, vol. 363, No. 6430, Jun. 17, 1993, pp. 603-604.
Pan, et al., "Very long carbon nanotubes", Nature, vol. 394, No. 6694, Aug. 13, 1998, p. 631-632.
Collins, et al., "Nanotube Nanodevice", Science, vol. 278, Oct. 3, 1997, pp. 100-102.
De Heer, et al., "A Carbon Nanotube Field-Emission Electron Source", Science, vol. 270, Nov. 17, 1995, pp. 1179-1180.
Che, et al., "Carbon nanotubule membranes for electrochemical energy storage and production", Nature, vol. 393, No. 6683, May 28, 1998, pp. 346-348.
Calvert, "Nanotube composites: A recipe for strength", Nature, vol. 399, No. 6733, May 20, 1999, p. 210.
Baughman, et al., "Carbon nanotube actuators", Science, vol. 284, No. 5418, May 1999, pp. 1340-1344.
Modi, et al., "Miniaturized gas ionization sensors using carbon nanotubes", Letters to Nature, Nature, vol. 424, Jul. 10, 2003, pp. 171-174.
Downard, "Electrochemcially Assisted Covalent Modification of Carbon Electrodes", Electroanaysis, vol. 12, No. 14, 2000, pp. 1085-1096.
Pandurangappa, et al., "Homogeneous chemical derivatisation of carbon particles: a novel method for functionalising carbon surfaces", Analyst, vol. 127, No. 12, 2002, pp. 1568-1571.
Pandurangappa, et al., "Physical adsorption of N,N'-diphenyl-p-phenylenediamine onto carbon particles: Application to the detection of sulfide", Analyst, vol. 128, 2003, pp. 473-479.

(56) References Cited

OTHER PUBLICATIONS

Wildgoose, G. et al., "Anthraquinone-derivatised carbon powder: reagentless voltammetric pH electrodes", Talanta, vol. 60, No. 5, Jul. 27, 2003, pp. 887-893.

Aso, et al., "Cationic polymerization and copolymerization of vinylferrocene", Macromolecular Chemistry, vol. 124, Issue 1, May 22, 1969, pp. 232-240.

Nuyken, et al., "Anionic homo- and block copolymerization of vinylferrocene", Macromolecular Chemistry and Physics, vol. 198, Issue 11, Nov. 1997, pp. 3353-3363.

Lai, et al., "Free-radical homopolymerization and copolymerization of vinylferrocene", Journal of Polymer Science Part A-1: Polymer Chemistry, vol. 9, Issue 3, Mar. 1971, pp. 651-662.

Baumert, et al., "Styrene-vinylferrocene random and block copolymers by TEMPO-mediated radical polymerization", Macromolecular Rapid Communications, vol. 20, Issue 4, Apr. 1999, pp. 203-209.

Kuramoto, et al., "Thermosensitive and redox-active polymers: Preparation and properties of poly(N-ethylacrylamide-co-vinylferrocene) and poly(N,N-diethylacrylamide-co-vinylferrocene)", Journal of Polymer Science Part A: Polymer Chemistry, vol. 35, Issue 10, Jul. 30, 1997, pp. 1967-1972.

Yang, et al., "Novel Synthesis and Characterization of Side-Chain Ferrocene-Containing Polymers", Macromolecules, 2002, vol. 35, No. 9, 2002, pp. 3426-3432.

Senthil, et al., "Studies on the mesomorphic properties of ferrocenylene-based organophosphorous liquid-crystalline polymers containing phenyl and biphenyl pendant units", Journal of Applied Polymer Science, vol. 85, Issue 4, Jul. 25, 2002, pp. 831-841.

Wright, et al., "Organometallic Nonlinear Optical Polymers. 4. Organometallic Main-Chain, Side-Chain, and Guest-Host Polymers: A Study of Their Orientation and Relaxation Using Second Harmonic Generation", Macromolecules, vol. 27, No. 11, 1994, pp. 3016-3022.

Casado, et al., "Siloxane and Organosilicon Dimers, Monomers, and Polymers with Amide-Linked Ferrocenyl Moieties. Synthesis, Characterization, and Redox Properties", Inorganic Chemistry, vol. 34, No. 7, 1995, pp. 1668-1680.

Gonsalves, et al., "Ferrocene-containing polyamides and polyureas", Journal of the American Chemical Society, vol. 106, No. 13, 1984, pp. 3862-3863.

Nuyken, et al., "Novel sulfur-containing ferrocene polymers", Macromolecular Chemistry and Physics, vol. 197, Issue 10, Oct. 1996, pp. 3343-3354.

Nelson, et al., "Thermal Ring-Opening Polymerization of Hydrocarbon-Bridged [2]Ferrocenophanes: Synthesis and Properties of Poly(ferrocenylethylene)s and Their Charge-Transfer Polymer Salts with Tetracyanoethylene", Chemistry—A European Journal, vol. 3, Issue 4, Apr. 1997, pp. 573-584.

Turrin, et al., "Behavior of an Optically Active Ferrocene Chiral Shell Located within Phosphorus-Containing Dendrimers", Organometallics, vol. 21, No. 9, 2002, pp. 1891-1897.

Takeuchi, et al., "Accelerated free-radical copolymerization of 9-vinylanthracene with methyl methacrylate using ethylaluminium sesquichloride", Macromolecular Chemistry and Physics, Rapid Communications, vol. 10, Issue 12, Dec. 1989, pp. 645-648.

Katz, "Polymerization and copolymerization of 1- and 9-vinylanthracenes and 9-vinylphenanthrene", Journal of Polymer Science Part A: General Papers, vol. 1, Issue 5, May 1963, pp. 1635-1643.

Krakovyak, et al., "Investigation of polymerization and copolymerization of 9-vinyl-anthracenes", European Polymer Journal, vol. 10, Issue 8, Aug. 1974, pp. 685-692.

Tiera, et al., "Fluorescence study of the interaction between metal ions and methyl methacrylate-methacrylic acid copolymers in aqueous solutions: thallium(I), calcium(II), and terbium(III)", Colloid and Polymer Science, vol. 276, Issue 3, Mar. 1998, pp. 206-212.

Zhang, et al., "9-(Guanidinomethyl)-10-vinylanthracene: a suitable fluorescent monomer for MIPs", Tetrahedron Letters, vol. 42, Issue 26, Jun. 25, 2001, pp. 4413-4416.

De Andrade, "Dynamic and Static Fluorescence Spectroscopy Applied to Miscibility of Poly(n-butyl methacrylate-co-styrene) with Polystyrene and Morphological Analysis by Epifluorescence Microscopy", The Journal of Physical Chemistry B, vol. 108, No. 13, 2004, pp. 3975-3984.

Rabjohns, et al., "Synthesis of aromatic polyamides containing anthracene units via a precursor polymer approach", Polymer, vol. 38, Issue 13, 1997, pp. 3395-3407.

Liu, et al., "Fullerene Pipes", Science, vol. 280, 1998, pp. 1253-1256.

Yao, et al., "Polymerization from the Surface of Single-Walled Carbon Nanotubes—Preparation and Characterization of Nanocomposites", Journal of the American Chemical Society, vol. 125, Issue 51, Dec. 2, 2003, pp. 16015-16024.

\* cited by examiner

ELECTROCHEMICAL SENSORS

CROSS-REFERENCE TO RELATED APPLICATIONS

This application claims priority as a 35 USC 371 application to PCT application PCT/IB2012/057638 filed 21 Dec. 2012 which claims priority to GB application 1122301.3 filed 23 Dec. 2011. The disclosures of both applications above are incorporated by reference herein in their entireties.

FIELD AND BACKGROUND

This invention relates to electrochemical sensors for determining an analyte in a fluid. There are numerous circumstances in which it is desirable to detect, measure or monitor a constituent of a fluid. One of the commonest requirements is to determine hydrogen ion concentration (generally expressed on the logarithmic pH scale) of aqueous fluids which may for example be a water supply or an effluent. Another requirement of interest is the determination of hydrogen sulfide or thiols. Electrochemical sensors may be used for such a purpose and the electrochemistry may incorporate a redox-active species whose oxidation and/or reduction is monitored as a part of the analysis. One approach is to locate redox active species at the surface of an electrode, although redox active species may also be used in solution.

For instance to measure pH, WO 2005/066618 disclosed an electrochemical sensor in which the electrochemical cell contains two organic compounds which are pH-sensitive redox systems and a ferrocene compound as an internal reference which is not sensitive to pH. To measure sulfide, WO2001/063094 and WO2004/011929 described an approach in which electrochemistry is coupled through a mediator compound to sulfide which is the intended analyte. This mediator compound is present in an electrochemical cell which is exposed to the sulfide. An electrochemical oxidation and reduction of the mediator compound can take place when appropriate electrical potential is applied to the electrodes. However, one of the redox reactions of the mediator compound can also be brought about through a chemical reaction with the sulfide, and when this takes place there is a measurable change to the electrochemistry. Ferrocene carboxylate and sulfonate were suggested as mediator compounds in Electroanalysis vol 18 pages 1658-63 (2006) and in Electrochimica Acta vol 52 pages 499-50 (2006). A number of ferrocene sulfonates for possible use in this way have been described in Journal of Organometallic Chemistry vol 692 pages 5173-82 (2007).

An issue which can arise in connection with electrochemical analytical systems is the stability of the redox active species employed, in particular stability when exposed to elevated temperatures during use. Exposure to elevated temperature may, however, be unavoidable when using an electrochemical sensor to monitor an industrial process.

A number of uses of sensors may expose them to temperatures which are above ambient temperatures at the earth's surface. One arises when carrying out analysis of fluids encountered downhole in a wellbore where it may be desirable to determine the concentration of analytes including hydrogen ions (pH=−log [concentration of H$^+$]) and H$_2$S.

As explained in a review article by Heo et al J. Organomet Chem vol 578 page 31 (1999), the term "ferrocenophane" has been applied to two categories of molecules. One category is molecules with a plurality of ferrocene units connected by one or more bridging groups connecting a cyclopentadiene ring of one ferrocene to a cyclopentadiene ring of another ferrocene. Two examples of such structures are:

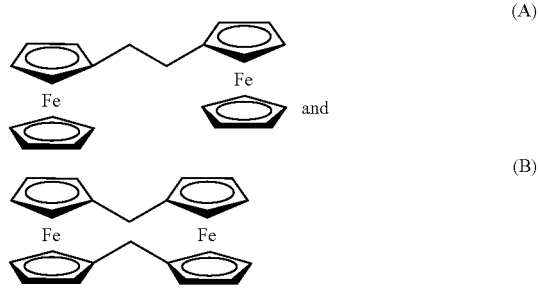

The other category of ferrocenophane has at least one bridging group connecting the two cyclopentadiene rings associated with a single iron atom. Two examples of such structures are

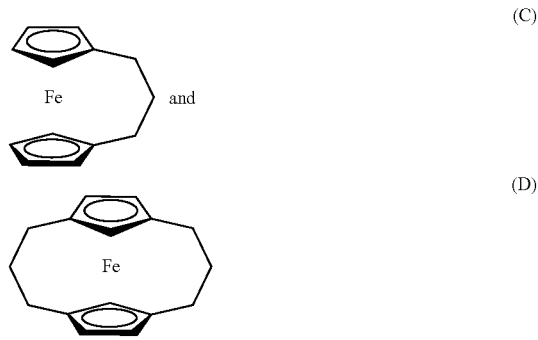

The structure (C) at the left has one bridging group directly connecting the two cyclopentadiene rings. The structure (D) at the right has two such groups. These bridging group are shown here as formed from carbon and hydrogen atoms only, so that the two cyclopentadiene rings are connected by an all-carbon chain but known bridging groups may include hetero atoms, notably non-metallic heteroatoms such as oxygen or nitrogen, in the chain.

It will be appreciated that the structure (B) above has two ferrocenes joined together in such a way that there is a bridge which (rather indirectly) connects the two cyclopentadiene rings associated with each iron atom, although it is an extended bridge which includes the other ferrocene group.

Cui et al Polyhedron vol 29 page 1697 (2010) described a ferrocenophane in which a bridging group extending between the two cyclopentadiene rings associated with a single iron atom was formed using 1,2-diaminocyclohexane, so that the chain of atoms between the two rings included two amine groups. They investigated the electrochemistry and demonstrated that these amine groups could participate in an overall redox reaction of the molecule. They also demonstrated that this bridging group could complex with metal cations and that this would affect the electrochemical potential of redox reactions of the ferrocene group. Sola et al Inorganic Chemistry vol 50 page 4212 (2011) made a similar finding with anions associating with a ferrocenophane in which the bridging group was guanidine attached to a chromogenic nitrophenyl group. Both Cui et al and Solo et al worked with added ions in amounts which were less than the stoichiometric amounts for 1:1 association with the ferrocenophane.

SUMMARY

We have now found that ferrocenophanes in the category where at least one bridging group connects two cyclopentadiene rings associated with the same iron atom can be used in measuring the concentration of an analyte and can give an enhanced working life and/or increased tolerance to temperature compared with ferrocene compounds without any bridging group connecting their cyclopentadiene rings.

In a first aspect there is provided an electrochemical sensor for an analyte (which may possibly be hydrogen ions, hydrogen sulfide or thiols) incorporating a compound which comprises a ferrocenophane with at least one bridging group covalently attached to and connecting the two cyclopentadiene rings associated with a single iron atom. A second aspect provides a method of determining the concentration of an analyte in a liquid by an electrochemical measurement in the presence of such a compound comprising a ferrocenophane. In various embodiments the compound comprising a ferrocenophane may be a ferrocenophane with at least one substituent on a cyclopentadiene ring or a compound with a ferrocenophane group attached to some other compound. It may be in solution in an electrolyte but it is also possible that the ferrocenophane is immobilized to a solid, electrically conductive substrate.

If the ferrocenophane-containing compound is immobilized to a substrate, this substrate may be a form of conductive carbon. This carbon may be in particulate form, for instance powdered graphite, in which case the particulate carbon may in turn be immobilized as part of a conducting electrode.

A bridging group connecting two cyclopentadiene rings in a ferrocenophane may include atoms other than carbon, and if so these other atoms maybe non-metals such as oxygen or nitrogen. However, in some embodiments of this invention the bridging group comprises only carbon, hydrogen and oxygen or even contains carbon and hydrogen only. In some embodiments the chain of atoms between the two cyclopentadiene rings made be a continuous chain of at least three carbon atoms carbon atoms or possibly a chain of at least three atoms consisting of carbon atoms and one or more ether oxygen atoms. The ferrocenophane containing compound may comprise at least one ionic group.

When the concentration of an analyte is to be measured, the absolute quantity of solution containing the analyte and hence the absolute quantity of analyte which is available for contact with a sensor are separate parameters which may be unknown. In some embodiments, measurement of the concentration of analyte may be carried out with a small quantity of ferrocenophane-containing compound brought into contact with a relatively large quantity of liquid containing the analyte. Consequently, the molar quantity of analyte which would be available for contact with the ferrocenophane may be many times greater (for instance more than 100 times greater) than the molar quantity of ferrocenophane.

It is an advantage of some embodiments that the atoms of the bridging group(s) are such that a bridging group does not undergo reaction or association with analyte nor with ionic species which are not the intended analyte but which happen to be present. This can be advantageous in avoiding dependence on absolute quantity of analyte available and avoiding unwanted disturbance of the electrochemical reaction(s) used to make a quantitative determination of analyte concentration.

When a ferrocenophane-containing compound is used in accordance with this invention, it may function in a similar way to a ferrocene compound. Thus it may undergo a redox reaction which is observed by an electrochemical measurement. Measurement may be a voltammetric procedure in which varying potential is applied to electrodes and current flow at the applied potential is recorded. Accordingly, the electrochemical sensor incorporating the ferrocenophane containing compound may comprise means to apply variable voltage to the sensor and measure current while the voltage is systematically varied.

In some embodiments, the ferrocenophane-containing compound is used as a reference compound which is insensitive to analyte concentration. Thus an electrochemical sensor used for voltammetric determination of an analyte, which may be hydrogen ions, may comprise at least one redox active compound which is able to participate in an electrochemical reaction of an analyte at a potential which is sensitive to the concentration of the analyte and also comprise a ferrocenophane as a reference which undergoes an electrochemical redox reaction at a potential which is substantially insensitive to the concentration of the analyte.

In some embodiments, an electrochemical reaction of the ferrocenophane group is linked to a reaction of the analyte, which may be hydrogen sulfide or thiols, so that current flow is proportional to analyte concentration.

DETAILED DESCRIPTION

Figure 1:
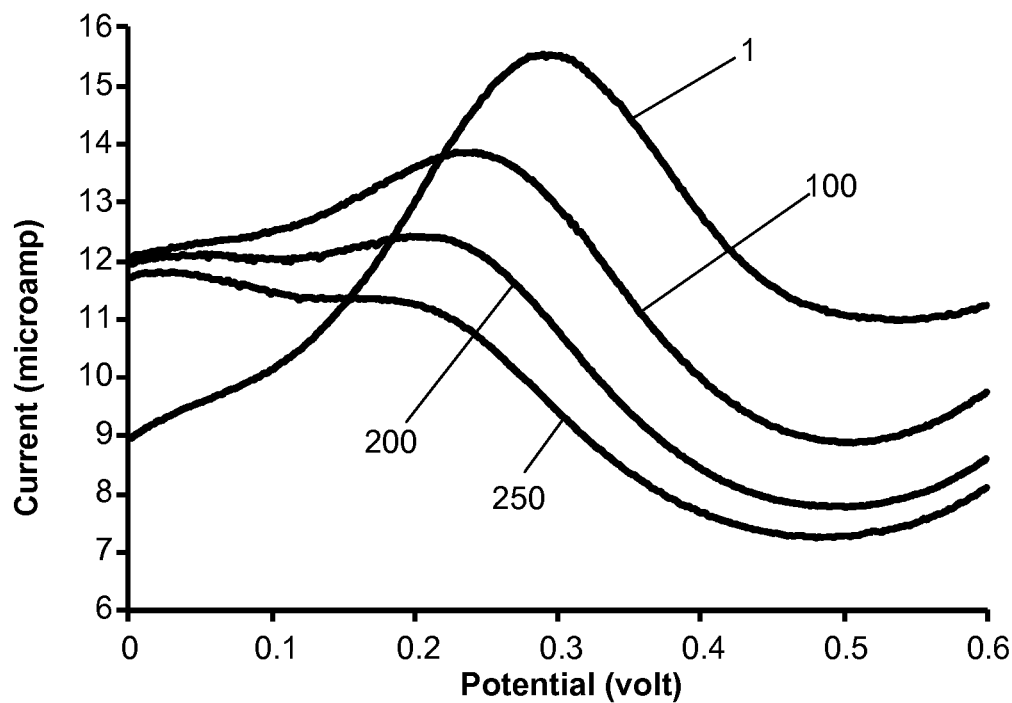
FIG. 1 shows voltammograms of 4-(6-[3]ferrocenophanylhexoxy)benzyl moieties immobilized on graphite, obtained in Example 6.

A ferrocenophane with one bridging group between the cyclopentadiene rings can be represented by the general formula

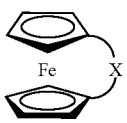

where X is a bridging group. In ferrocene itself the two cyclopentadiene rings lie parallel to each other and the spacing of 3.32 Angstroms between the rings is such that a chain of four atoms with simple sigma bonds between them, (as in a tetramethylene chain for instance) would connect the rings while allowing them to remain coplanar. A chain of three carbon atoms is shorter and would pull the rings out of their normal parallel state so that they are tilted relative to each other.

Contrary to what might be expected, we have found that a ferrocenophane with the rings joined by a chain of three carbon atoms can display significantly greater stability than a ferrocene compound which does not have its rings joined together.

Therefore, in some embodiments a bridging group provides a chain of three or more atoms connecting the cyclopentadiene rings. The number of atoms in the chain may be greater than three and may range from three to five or three to six atoms. Longer chains are also possible. In some embodiments the chain between the two rings is a chain of carbon atoms and it may be an alkylene chain such as a poly-methylene chain containing from three to six carbon atoms.

In some embodiments a molecule may contain a ferrocenophane group covalently attached to another part of the overall molecule. In some embodiments a compound may be a ferrocenophane having one or more polar substituents. Such substituents may increase solubility in water or polar solvents such as acetonitrile. A substituent on ferrocenophane may be a substituent on one of the cyclopentadiene rings, for instance a sulfonate group which can be introduced by sulfonation of a ferrocenophane group in a manner analogous to the sulfonation of ferrocene.

It would be possible to attach a ferrocenophane group to a redox active aromatic compound which is a quinone or a hydroxyl amino compound thus forming a molecule with a pH sensitive redox group and also the redox active but pH insensitive ferrocenophane group to act as an internal reference analogously to the compounds with ferrocene groups which are exemplified in US 2011/0162977.

Synthetic routes for making ferrocenophanes are available in the literature. Rosenblum et al J. Amer. Chem. Soc. vol 85 page 316 (1963) reviewed several methods of synthesis of ferrocenophanes. In a number of instances the starting material was ferrocene with a carboxaldehyde substituent group on one of the cyclopentadiene rings.

The synthesis of a ferrocenophane by reacting iron(III) chloride with an iron-free molecule having two cyclopentadiene rings joined by a bridging group has been reported by Lutteringhaus and Kullick in Angew. Chemie vol 58 page 438 (19548). The yield was only 2.5%.

A ferrocenophane with a tetramethylene chain between the cyclopentadiene rings can be prepared from a ferrocenophane with a three carbon bridge where one carbon atom of the bridge is a carbonyl group, using diazomethane to lengthen the chain from three to four carbon atoms, followed by reduction of the keton group. This route was mentioned by Rosenblum et al above and has been used by Hisatome et al J. Organomet. Chem vol 107 page 87 (1976) to prepare ferrocenophanes in which the cyclopentadiene rings were joined by multiple tetramethylene bridges.

An electrochemical sensor may contain a ferrocenophane compound in solution. For instance a sensor may have electrodes in contact with a body of liquid retained by a membrane which is permeable to the analyte, as illustrated in U.S. Pat. No. 7,758,734 for example. With such an arrangement the ferrocenophane compound could be in solution in the liquid retained by the membrane. The liquid could be aqueous or it could be a polar non-aqueous solvent such as acetonitrile.

In some embodiments a compound comprising a ferrocenophane group is placed on a conductive solid substrate which may be a form of conductive carbon, possibly a carbon electrode. A compound may for instance be deposited on a carbon substrate through evaporation of a droplet of solution or suspension placed on the surface of a carbon electrode. Another method is abrasive immobilisation as referred to in Scholz, F. and Meyer, B. "Voltammetry of Solid Microparticles Immobilised on Electrode Surfaces in Electroanalytical Chemistry" ed. A. J. Bard, and I. Rubenstein, Marcel Dekker, New York, vol 20 page 1 (1998). In this procedure the electrode is polished with glass polish paper (H00/240) and then with silicon carbide paper (P1000C) for smoothness. The derivatised carbons are then immobilised onto the electrode by gently rubbing the electrode surface on a fine filter paper containing the derivatized carbon particles.

Another possibility is that a ferrocenophane is immobilized on a substrate surface by chemical reaction. One method which may be used for the attachment of a ferrocenophane to a carbon substrate is the method described in WO 2010/106404 in which a strong base is used to form a reactive carbene which attaches to a carbon surface.

Another method for chemical immobilization onto a substrate is the subject of a recent GB patent application number GB1122043.1 filed 21 Dec. 2011 (applicants' file reference IS11-0588, the disclosure of which is incorporated by reference). This method comprises exposing the carbon surface to a reaction mixture containing a thiol (also termed a mercaptan) and a free radical initiator. The reaction can be depicted in general terms as

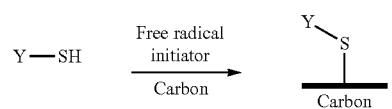

Energy may be supplied to decompose the free radical initiator and thereby release free radicals to bring about the reaction. This may be done by exposure to light, such as an ultra violet light source, or may be done by heating to a moderate temperature. The moiety Y—S— becomes covalently attached to the carbon surface. This moiety can incorporate a ferrocenophane group. The reaction may be carried out with the thiol and the free radical initiator in solution or dispersed as a suspension in a liquid. In some embodiments the reaction is carried out in solution in an aprotic solvent which is anhydrous.

The free radical initiator will generally be a compound which decomposes under mild conditions to form free radicals. A number of such compounds are available and may be compounds known for use as free radical initiators of polymerisation reactions. One class of such materials are azo compounds having a general formula R—N=N—R.

These can decompose on heating to liberate R. free radicals and nitrogen. Another class of such molecules is organic peroxides which rupture at the oxygen to oxygen bond. This may be followed by decomposition to more stable carbon centred free radicals. In some embodiments, the thiol and the free radical initiator are in stoichiometric quantities, or there is an excess of the free radical initiator, so as to bring about complete reaction of the thiol.

A further method for chemical immobilization onto a substrate is also the subject of a recent GB patent application number GB1122050.6 filed 21 Dec. 2011 (Applicants' file reference IS11-1013 the disclosure of which is incorporated by reference). This comprises exposing the carbon surface to an aprotic solvent containing a hydrazone molecule of the general formula

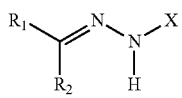

or the corresponding salt of formula

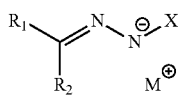

and decomposing the hydrazone so that nitrogen is released and a reactive carbene moiety

is formed and becomes covalently attached to the carbon surface.

The groups $R_1$ and $R_2$ which become attached to the carbon surface may be the same or different. $R_1$ may incorporate a ferrocenophane group while $R_2$ (but not $R_1$) may simply be hydrogen. The group X denotes a group which leaves as $X^-$ when a covalent sigma bond to nitrogen is broken. It may be a group recognised to be a good leaving group such as an aryl sulfonyl group.

The hydrazone of general formula

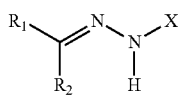

may conveniently be made by condensation of an aldehyde of the formula $R_1R_2CHO$ and a hydrazide of the formula $H_2N—NH—X$. The condensation reaction will generally be followed by conversion of the hydrazone into salt form, by reaction with a base such as sodium methoxide.

Decomposition of the hydrazone to bring about carbene formation and derivitisation of carbon may done in several ways. One possibility is to supply energy to the reaction mixture by heating it. Another is to supply energy by irradiating with ultra-violet light and so causing photolytic decomposition.

Elemental carbon to which a ferrocenophane-containing compound is attached may have a variety of forms including graphite powder, glassy carbon, carbon fibres, carbon black or carbon paste, boron doped diamond and carbon epoxy. A further form of carbon is the carbon nanotube (CNT) which was discovered in 1991. The structure of carbon nanotubes approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other. A yet further form of carbon which may be derivatized is graphene which may be in the form of graphene flakes and after derivitization these flakes may be immobilized on a conductive substrate. These forms of carbon are solids, and may be particulate solids.

If a ferrocenophane-containing compound is chemically attached to particulate carbon, this derivatized carbon may be immobilized on a carbon electrode. This may be done, as in the examples above, by evaporation of a suspension of the particles in a volatile solvent.

Another possibility is to pack such derivatized particulate carbon into a recessed cavity in an electrode. The empty recess might be filled with the derivatized carbon powder which would be mechanically compacted. The resulting void in the recess would then be refilled and compacted again. This would be repeated several times until the recess is full. The material would be pressed such that the carbon particles are packed into a dense matrix.

A further possibility is that derivatized carbon particles may be screen printed onto a substrate which may be an insulating material. Carbon particles derivatized with a second redox active compound which is insensitive to analyte/pH and which acts as a reference may be screen printed onto the same or another substrate. The particulate carbon may be combined with a binding material, which may be a conductive binding material such as a graphite-containing ink, and then screen printed onto the electrode. An external reference electrode may possibly be used with such a screen-printed electrode. One possible external reference is a silver/silver-chloride electrode. A screen-printed electrode may possibly carry such an external reference electrode on a portion of an insulating substrate. Particulate carbon derivatized with a redox active compound, mixed with a binder may also be applied to a working electrode by an inkjet-type process as an alternative to screen printing.

A screen-printed electrode may possibly be covered with a polymer film or coating. The polymer film or coating may, among other things, make the electrode more robust, prevent external adverse effects of the redox active compound(s), and allow for sterilization of the electrode without affecting the functionality of the electrode.

An electrode on which a compound comprising a compound comprising a ferrocenophane is immobilised may be the working electrode of a two or three electrode electrochemical cell. Measurement using such an electrochemical cell may be carried out by cyclic voltammetry or square wave voltammetry which are well established techniques in which a progressively varying potential is applied to an electrode and the current flow is recorded.

Example 1

Comparative

This example demonstrates that t-butyl ferrocene sulfonate, which is a ferrocene compound without any bridging group to join its cyclopentadiene rings, decomposes at elevated temperature by disproportionation of the ferrocene to form cyclopentadiene, potassium tert-butyl cyclopentadiene sulfonate and iron oxide, thus:

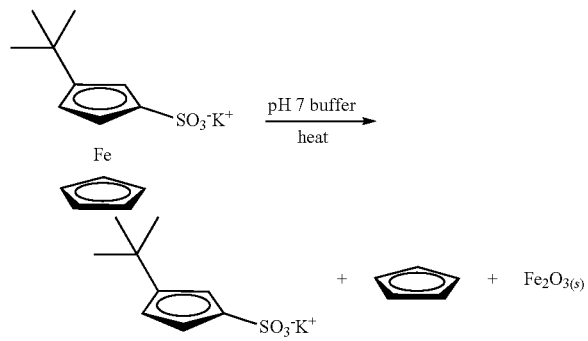

Potassium tert-butylferrocene sulfonate, 1 mmol in pH7 buffer, was purged with nitrogen for 20 mins, sealed and heated at 120° C. for 24 hr and the solution analysed by headspace GC/MS. Cyclopentadiene was detected in the headspace and iron oxide was observed as a brown deposit from the solution. This indicates that the iron was being displaced from the compound on heating.

An analogous experiment was conducted with ferrocene monosulfonate. The gas chromatogram showed a peak at a retention time of 3.33 minutes due to cyclopentadiene and a smaller peak at a retention time of 16.11 minutes due to dicyclopentadiene.

Example 2

A ferrocenophane with a trimethylene chain between the two cyclopentadiene rings, designated [3]ferrocenophane, was synthesised from commercially available ferrocene carboxaldehyde in four steps as outlined by the following reaction scheme which is based on a procedure described by Rosenblum et al in J. Amer. Chem. Soc. vol 85 p 316 (1963).

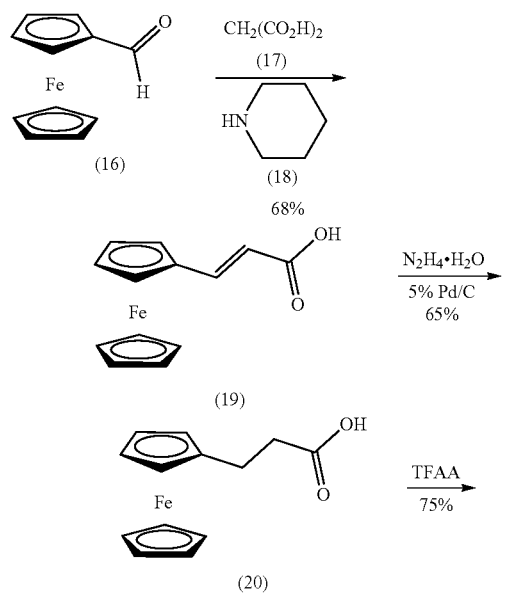

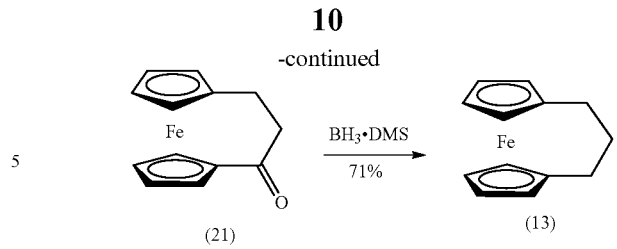

In the first step of the above scheme, Doebner modification of the Knoevenagel condensation of ferrocene carboxaldehyde (16) with malonic acid (17) was catalysed by piperidine (18). Ferrocene carboxaldehyde (16) (6.4 g, 30 mmol), malonic acid (17) (3.12 g, 30 mmol), and piperidine (20 drops) (18) were added to pyridine (12 ml) and heated at reflux for 2 hr. The reaction was cooled, poured into water (50 ml) and adjusted to pH1 with 5M HCl. The solid was filtered, washed with $H_2O$ and diethyl ether and dried to give β-ferrocenylacrylic acid (19), 5.22 g (68%).

Next, catalytic transfer hydrogenation was carried out using hydrazine hydrate as the hydrogen donor. β-Ferrocenylacrylic acid (19) (1.17 g, 4.57 mmol) was dissolved in ethanol (20 ml). 5% Palladium on carbon (50% $H_2O$) was added and the reaction heated to reflux. Hydrazine monohydrate (0.7 ml) was added and suspension heated for 30 min. More hydrazine monohydrate (0.5 ml) was added and suspension heated for 3 hr. More hydrazine monohydrate (1 ml) was added and suspension heated for 1.5 hr and finally hydrazine monohydrate (1 ml) was added and suspension heated for 2 hr. The total volume of hydrazine monohydrate added was 3.2 mls and heated at reflux lasted 7 hr in all. The suspension was cooled slightly, filtered through a pad of celite and the filtrate evaporated. Acetone was added to the residue to destroy residual hydrazine monohydrate in an exothermic reaction. Solvent was evaporated, the residue was suspended in $H_2O$ and 15% HCl was added. The product was extracted into diethyl ether, the combined organic phase extracted with dilute HCl, $H_2O$ and brine, then dried over $MgSO_4$ to give ferrocenylpropionic acid (20), 765 mg (65% yield).

Next, formation of the mixed anhydride with trifluoroacetic anhydride (TFAA) followed by ring closure gave [3]ferrocenophane-1-one (21). Ferrocenylpropionic acid (20), 765 mg (2.96 mmol) was dissolved in dichloromethane and cooled to 0° C. Trifluoroacetic anhydride (0.9 ml, 6.47 mmol) was added and stirred at 0° C. for 5 hr. The reaction mixture was poured into aqueous $NaHCO_3$ and effervescence was observed. The organic phase was removed, and extracted with aqueous $NaHCO_3$ $H_2O$ and brine, and dried over $MgSO_4$ and the solvent removed by evaporation. The crude product was purified by column chromatography, eluting with 10-15% ethyl acetate in hexane to give [3]ferrocenophane-1-one (21), 533 mg, (75%).

In the fourth stage of the synthesis, [3]ferrocenophane-1-one (21), (2.74 g, 11.4 mmol) was dissolved in dichloromethane and 1M borane-dimethyl sulfide complex in dichloromethane (11.3 ml, 11.3 mmol) was added dropwise. Effervescence was observed. The reaction was stirred at ambient temperature for 3 hr then quenched into aqueous $NH_4Cl$. The organic phase was removed and extracted with $H_2O$ and brine, dried over $MgSO_4$ and the solvent removed. The resultant crude product was purified by column chromatography, eluted with hexane to give [3]ferrocenophane (13), 1.83 g (71%). This was an overall yield of 23%.

The Rosenblum and Hisatome literature references mentioned earlier teach the conversion of [3]ferrocenophane-1- one (21) to [4]ferrocenophane by reaction with diazomethane to lengthen the chain and reduction of the keto group with lithium aluminium hydride, thus:

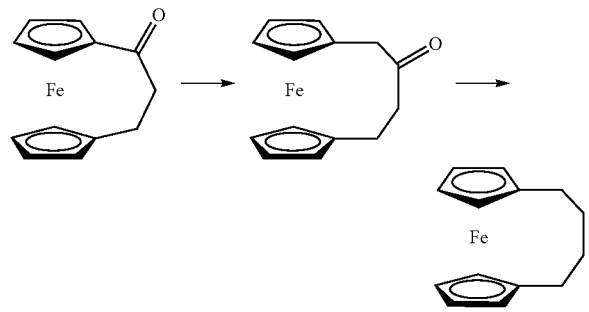

Example 3

[3]Ferrocenophane prepared as in Example 2 was sulfonated using chlorosulfonic acid in acetic anhydride and neutralized to the potassium salt (36) thus:

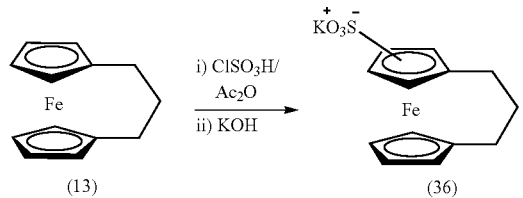

[3]Ferrocenophane (13) (339 mg, 1.5 mmol) was dissolved in acetic anhydride and cooled in an ice-bath. Chlorosulfonic acid (175 mg, 1.5 mmol) was added and the solution stirred at 5° C. for 30 mins then at ambient temperature for 1.5 hr. Thin layer chromatography indicated that some [3]ferrocenophane (13) remained. More chlorosulfonic acid (1 drop) was added and stirred for further 2 hr. The reaction was poured into H2O (20 ml) and stirred for 1 hr, the solvent was removed by evaporation and the residue triturated with hexane to remove residual [3]ferrocenophane (13) The solid was dissolved in H2O, the pH adjusted to pH5 with aqueous KOH and the solvent removed and the residue triturated with EtOH to remove H2O. The solid was dissolved in EtOH, filtered and the filtrate evaporated to give potassium [3]ferrocenophane sulfonate (36).

Example 4

The thermal stability of the [3]ferrocenophane sulfonate prepared in Example 3 was examined by heating a solution containing 0.5 mM of the ferroceneophane sulfonate dissolved in pH 7 phosphate buffer at various temperatures for a period of 24 hrs (unless otherwise stated) and comparing the voltammetric response at room temperature before and after heating.

Electrochemical measurements were recorded using a µAutolab or a PGSTAT 30 potentiostat (Ecochemie, Netherlands) with a standard three-electrode configuration dipping into the solution in pH 7 buffer. The three electrodes were a glassy carbon working electrode, a stainless steel rod as counter electrode and a saturated calomel electrode as the reference. Analysis of the relative peak currents allows the percentage of decay to be calculated. A comparative test was carried out using t-butylferrocene sulfonate.

Results are given in the following table

| Compound | % decay 120-125° C. | % decay at 150° C. or more |
| --- | --- | --- |
| KO₃S / t-butylferrocene | 21% after 24 hours at 120° C. | 70% after 24 hours at 120° C. |
| KO₃S / [3]ferrocenophane | Negligible after 24 hours at 125° C. 10% after 90 hours at 125° C. | 47% after 24 hours at 120° C. |

It can be clearly seen that the ferrocenophane sulfonate shows an improved thermal stability compared to the ferrocene sulfonate.

The cyclic voltammetric response of the ferrocenophane sulfonate was observed in the presence of increasing concentrations of added sulfide. As the sulfide concentration increased, there was an increase in the oxidative peak current and a corresponding decrease in the reductive peak current consistent with an electrocatalytic pathway. This was very similar to previous observations with ferrocene compounds, indicating that a ferroceneophane was suitable for use in an $H_2S$ sensor.

Example 5

A compound with ferrocenophane attached to a benzyl group was prepared from [3]ferrocenophane made according to Example 2 and immobilized on graphite by the method of WO2010/106404.

Friedel-Crafts acylation of [3]ferrocenophane (13) gave 6-(Bromohexyl)-1-oxo-[3]ferrocenophane (27) as a mixture of two isomers. This was reduced using borane-dimethylsulfide complex to give 6-(bromohexyl)-[3]ferrocenophane (28). 6-(Bromohexyl)-[3]ferrocenophane (28) was alkylated with 4-hydroxy benzaldehyde in the presence of potassium carbonate to give the aldehyde (29). The aldehyde functionality was reduced with sodium borohydride to give the benzyl alcohol (30). which was converted to the benzyl bromide (31) using phosphorus tribromide. The benzyl bromide (31) was subsequently immobilized using DBU to generate a reactive carbene which attached to graphite. The reaction scheme is shown below:

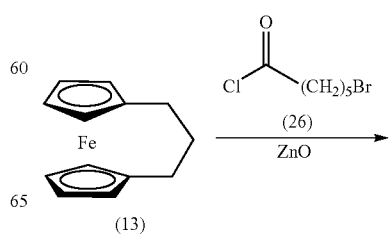

13

-continued

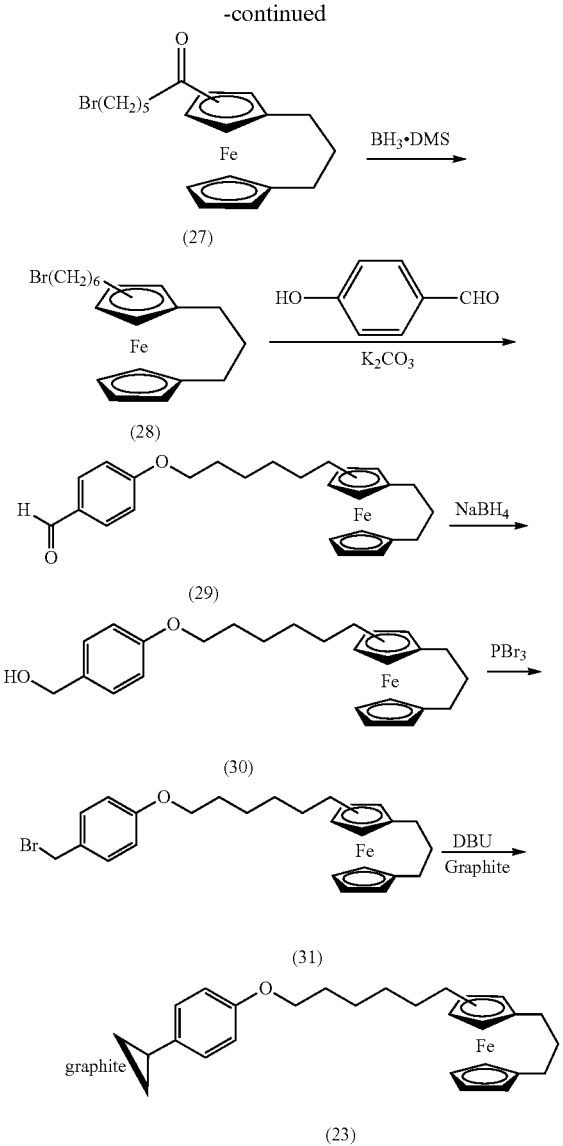

Details of the steps of this reaction scheme were as follows:

Synthesis of 6-(Bromohexyl)-1-oxo-[3]ferrocenophane (27)

[3]ferrocenophane (13) (103 mg, 0.45 mmol) was dissolved in CH$_2$Cl$_2$ and zinc oxide (44 mg, 0.54 mmol) was added. 6-Bromohexanoyl chloride (289 mg, 1.35 mmol) was added dropwise and the resultant red mixture stirred at ambient temperature overnight. The reaction was poured into iced water and the organic phase removed, extracted with aqueous Na$_2$CO$_3$, water and brine and dried over MgSO$_4$. The crude product was applied to a silica column and eluted with 10-15% ethyl acetate/hexane. Two materials eluted and analysis by GC/MS indicated that these were two isomers of 6-(Bromohexyl)-1-oxo-[3]ferrocenophane (27). The amounts obtained were first eluting isomer, 53 mg (29%); second eluting isomer, 90 mg (49%); total 140 mg (78%).

14

Synthesis of 6-(bromohexyl)-[3]ferrocenophane (28)

6-(Bromohexyl)-1-oxo-[3]ferrocenophane (27) (2.14 g, 5.3 mmol) was dissolved in dichloromethane (20 ml) and 1M borane-dimethylsulfide complex (5.2 ml, 5.2 mmol) was added dropwise; effervescence was observed. The reaction was stirred at ambient temperature for 16 hr. The reaction was poured into aqueousNH$_4$Cl and the organic phase removed. The organic phase was extracted with H$_2$O, brine, dried over MgSO$_4$ and the solvent removed. The crude material was purified by column chromatography eluting with 0-5% ethyl acetate in hexane to give 6-(bromohexyl)-[3]ferrocenophane (28), 1.4 g (68%).

Synthesis of 4-(6-[3]ferrocenophanylhexoxy)benzaldehyde (29)

6-(Bromohexyl)-[3]ferrocenophane (28) (321 mg, 0.82 mmol), 4-hydroxybenzaldehyde (201 mg, 1.72 mmol) and potassium carbonate (1 g, 7.2 mmol) were added to acetone (15 ml) and heated at reflux for 7 hr, cooled and aged at ambient temperature overnight; TLC indicated some 6-(bromohexyl)[3]-ferrocenophane (28) still present. The suspension was heated at reflux for a further 6 hrs. The solid was filtered, washed with acetone and the solvent removed. The crude product was purified by column chromatography eluted with 10% ethyl acetate in hexane to give 4-(6-[3]ferrocenophanylhexoxy)benzaldehyde (29), 225 mg (63% yield).

Synthesis of 4-(6-[3]ferrocenophanylhexoxy)benzyl alcohol (30)

4-(6-[3]Ferrocenophanylhexoxy)benzaldehyde (29) (513 mg, 1.19 mmol) was dissolved in CHCl$_3$/MeOH (3.5 ml/10 ml) and sodium borohydride (44 mg) added portionwise and stirred overnight at ambient temperature; effervescence was observed. TLC indicated trace amount of starting material (29) still present. Sodium borohydride (20 mg) added and reaction stirred for 1 hr; TLC indicated no change. The solvent was removed and the residue partitioned between 0.5M NaOH and ethyl acetate. The organic phase was removed, extracted with water and brine, dried over MgSO$_4$ and the solvent removed. The resultant oil was dissolved in CH$_2$Cl$_2$, applied to a silica column and eluted with 10-25% ethyl acetate hexane to give 4-(6-[3]ferrocenophanylhexoxy)benzyl alcohol (30) 394 mg (76% yield).

Synthesis 4-(6-[3]ferrocenophanylhexoxy)benzyl bromide (31)

4-(6-Ferrocenophanylhexoxy)benzyl alcohol (30) (368 mg. 0.85 mmol) was dissolved in toluene, cooled to 0° C. and PBr3 added. The reaction was stirred at 0° C. for 1 hr then and ambient temperature for 3 hr. The reaction was poured into aqueous NaHCO$_3$, the aqueous phase removed and extracted with ethyl acetate. The combined organic phase was backwashed with aqueous NaHCO$_3$, H$_2$O, and brine, dried over MgSO$_4$ and the solvent removed. The crude product was purified by column chromatography eluting with 10% ethyl acetate in hexane to give 4-(6-[3]ferrocenophanylhexoxy)benzyl bromide (31), 235 mg (55% yield).

Immobilisation of 4-(6-[3]ferrocenophanylhexoxy)benzyl bromide (31)

4-(6-[3]Ferrocenophanylhexoxy)benzyl bromide (31) (220 mg, 0.44 mmol) was dissolved in toluene (1 ml) and graphite powder of particle size <20μ (30 mg) was added together with 1,8-diazabicyclo[5.4.0]undec-7-ene (DBU) (0.4 ml, 2.6 mmol) and the suspension heated at 45° C. overnight. The derivatised graphite (23) was collected by centrifugation, washed sequentially with toluene, N,N'-dimethylformamide, de-ionised water, acetone and methanol and then dried.

Example 6

For use as a comparison, the compound 4-(6-ferrocenylhexoxy)benzyl bromide (41) was prepared, following the procedure of the previous example but starting with ferrocene in place of [3]ferrocenophane. This was then immobilized on graphite powder using DBU as in the previous example. The overall reaction scheme was:

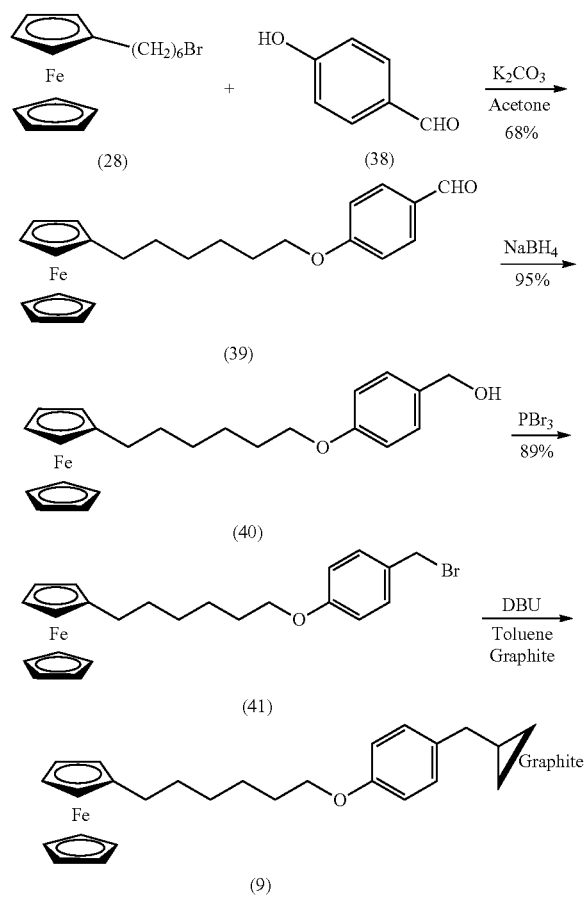

Figure 2:
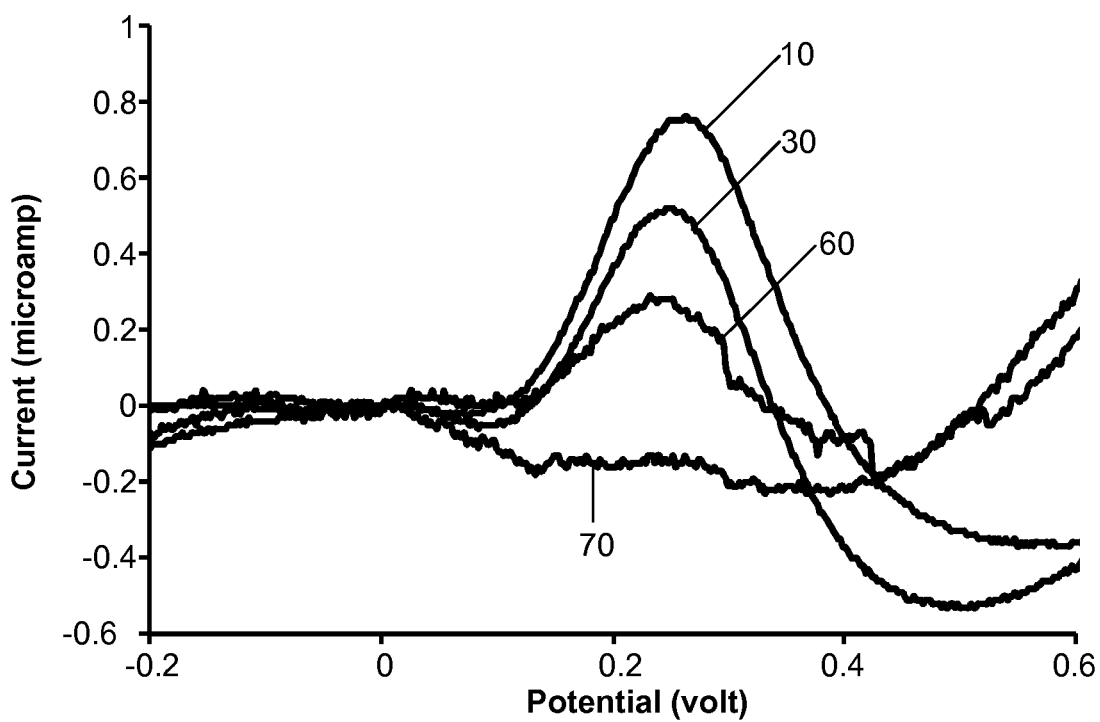
FIG. 2 shows voltammograms of the comparative 4-(6-ferrocenylhexoxy)benzyl moieties immobilized on graphite, also obtained in Example 6.

The electrochemistries of graphite (23) derivatized with a ferrocenophane compound according to Example 5 and the above ferrocene-derivatized graphite (9) were compared. In each case the derivatized graphite powder was suspended in a small amount of dichloromethane and a droplet of the suspension was placed on a glassy carbon electrode and allowed to evaporate, so as to deposit the derivatized graphite on the electrode surface. Square wave voltammetry in pH 7 phosphate buffer was then carried out at room temperature using the glassy carbon electrode as the working electrode and using a potentiostat, counter electrode and reference electrode as in Example 4. Voltammograms are shown as FIGS. 1 and 2, where the curves are marked with the number of scans carried out. with the number of scans carried out With the ferrocenophane-derivatized graphite (23) a current peak was observed at approximately +0.25 volt. The size of this peak diminished as scanning was repeated but as shown in FIG. 1 the peak was only slightly diminished after 100 scans and was still visible after about 200 scans. With the ferrocene-derivatized graphite (9) a current peak was again observed at approximately +0.25 volt as shown in FIG. 2. The size of this peak diminished more rapidly as scanning was repeated. The peak was still visible after 60 scans but became indistinguishable by 70 scans.

Example 7

A compound with ferrocenophane attached to a thiol group was prepared from [3]ferrocenophane made according to Example 2 and immobilized on graphite by reaction with a free radical initiator in the presence of graphite, in accordance with co-pending application GB 1122043.1 filed 21 Dec. 2011 (case reference IS11-0588).

Firstly, 6-(bromohexyl)-[3]ferrocenophane (28) was prepared from [3]ferrocenophane as in Example 5 above. Next, in accordance with the reaction scheme below, this was reacted with potassium thioacetate to give the thioacetate (32) which was then reduced with lithium aluminium hydride to give the thiol (24). The thiol (24) was attached to graphite in toluene, using 2,2'-azobis(2-methylpropionitrile) (AIBN) as the radical initiator, to give the modified graphite (25).

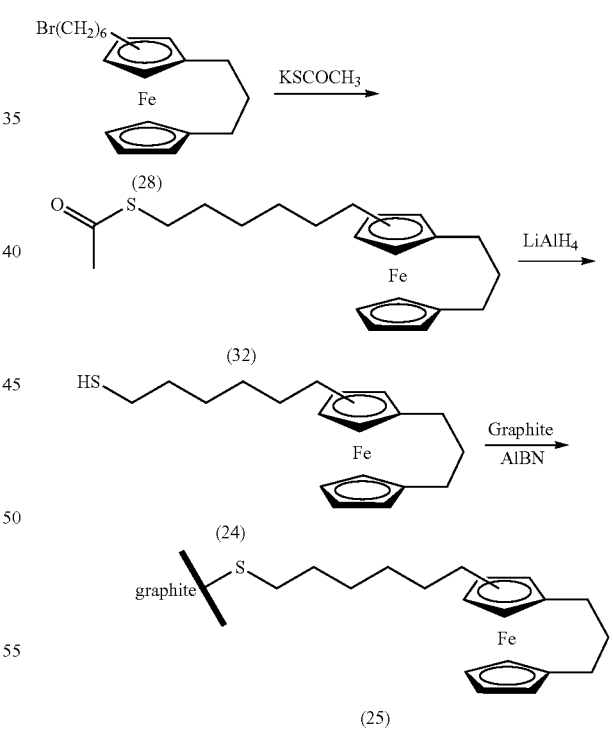

Details of the steps of this reaction scheme were as follows:

Synthesis of 6-([3]ferrocenophanyl)hexane thioacetate (32)

6-(Bromohexyl)-[3]ferrocenophane (28) (545 mg, 1.4 mmol) was dissolved in acetone (15 ml) and potassium thioacetate (483 mg, 4.23 mmol) added and the suspension heated at reflux for 3 hr. The suspension was cooled, the solid filtered and washed with acetone. The solvent was removed and the crude product purified by column chromatography eluded with 0-2% ethyl acetate in hexane to give 6-([3]-ferrocenophanyl)hexane thioacetate (32), 483 mg, (89% yield).

Synthesis of 6-([3]ferrocenophanyl)hexanethiol (24)

6-([3]-ferrocenophanyl)hexane thioacetate (32) (455 mg, 1.18 mmol) was dissolved in tetrahydrofuran (5 ml) and 1M lithium aluminium hydride (2.5 ml, 5 mmol) added dropwise; effervescence observed. The reaction was stirred at ambient temperature for 2 hr then poured in aqueous $NH_4Cl$ and the aqueous phase removed and extracted with ethyl acetate. The organic phase was extracted with $H_2O$, brine, dried over $MgSO_4$ and the solvent removed. The crude product was purified by column chromatography eluted with 0-2% ethyl acetate in hexane to give. 6-([3]ferrocenophanyl)hexanethiol (24), 368 mg (90% yield).

Immobilisation of 6-([3]ferrocenophanyl)hexanethiol (24)

6-([3]Ferrocenophanyl)hexanethiol (24) (87 mg, 0.25 mmol) was dissolved in 1,2-dichloroethane (1 ml). Graphite powder (15 mg) and 2,2'-azobis(2-methylpropionitrile) (AIBN 15 mg) were added and the suspension heated at 45° C. overnight. The derivatised graphite (25) was collected, washed sequentially with toluene, N,N'-dimethylformamide, de-ionised water and methanol and dried.

Example 8

For use as a comparison, the compound 6-ferrocenylhexanethiol was prepared, following the procedure of the previous example but starting with ferrocene in place of [3]ferrocenophane. This was then immobilized on graphite powder using ABIN as in the previous example. The immobilization step was:

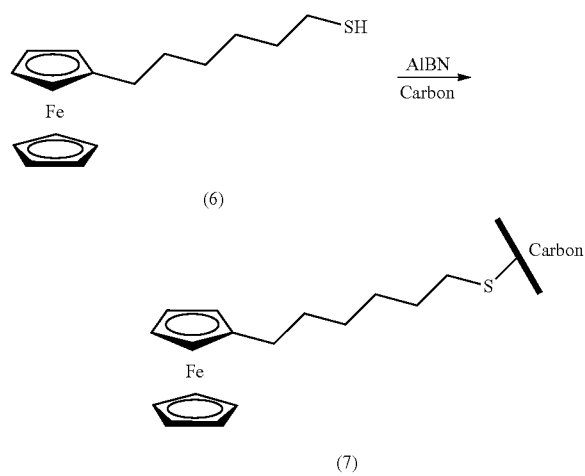

Figure 3:
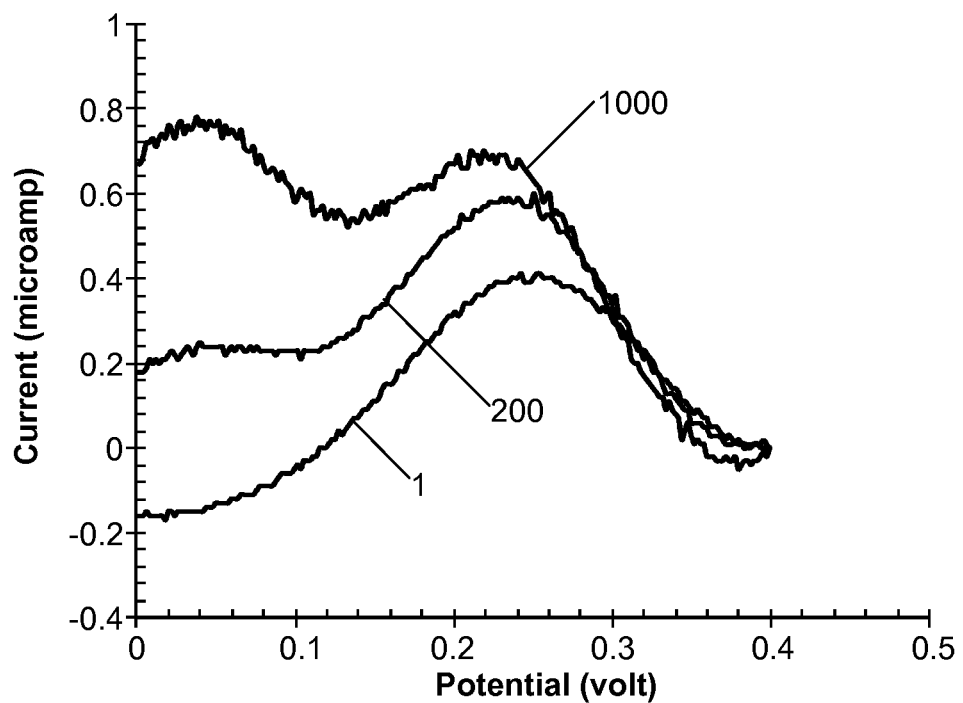
FIG. 3 shows voltammograms of 6-([3]ferrocenophanyl)hexanethio moieties immobilized on graphite, obtained in Example 8.
Figure 4:
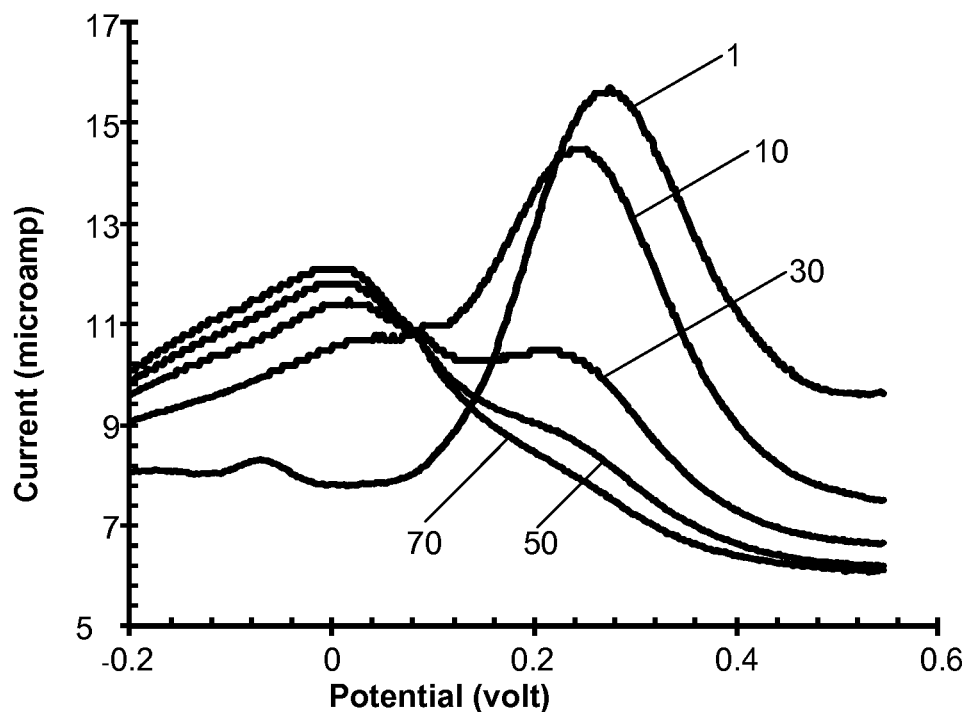
FIG. 4 shows voltammograms of the comparative 6-ferrocenylhexanethio moieties immobilized on graphite, obtained in Example 8.

The electrochemistries of graphite (25) derivatized with a ferrocenophane compound according to Example 5 and the above ferrocene-derivatized graphite (7) were compared. Once again, each derivatized graphite powder was suspended in a small amount of dichloromethane and a droplet of the suspension was placed on a glassy carbon electrode and allowed to evaporate, so as to deposit the derivatized graphite on the electrode surface. Square wave voltammetry in pH 7 phosphate buffer was then carried out at room temperature using the glassy carbon electrode as the working electrode and using a potentiostat, counter electrode and reference electrode as in Example 4. Voltammograms are shown as FIGS. 3 and 4. Once again the curves are marked to indicate the number of scans carried out.

With the ferrocenophane-derivatized graphite (25) a single current peak was observed at +0.23 V on the first scan. Scanning was repeated at one minute intervals and this peak at +0.23 volt slowly decayed. A new peak emerged between 0 and +0.1 volt. This was attributed to an electrochemical reaction of the graphite substrate itself. Although decay in the electrochemical signal was observed a clearly defined oxidative peak was still seen after 1000 scans. The experiment was repeated, carrying out the scans at 10 second intervals. Similar results were observed, showing that the electrochemical was dependent on the number of electrochemical scans, rather than on time in solution.

With the comparative ferrocene-derivatized graphite (7) a single current peak was observed at +0.24 volt on the first scan. This peak decayed on repeated scanning at one minute intervals and was barely detectable after 50 scans. It was entirely lost after 60 scans.

Operation of a pH Sensor

There are a number of redox active compounds which are sensitive to pH, so that when observed by voltammetry, the voltage at which there is maximum current flow (ie the voltage of the peak of the voltammetric wave) is dependent on pH. Such a compound can be used as a pH sensor and it may be immobilised on an electrode.

Aromatic quinones which have such redox reactions are disclosed in WO2005/066618. Aromatic nitro compounds, which undergo irreversible reduction to hydroxylamino and thereafter undergo pH dependent reversible oxidation from hydroxylamino to nitroso compounds are disclosed in WO2010/001082.

In contrast, the oxidative and reductive peaks for a ferrocenophane group, like those for ferrocene, are substantially independent of applied voltage, so a ferrocenophane-containing compound can serve as a reference when measuring pH. If the pH-sensitive compound and the ferrocenophane-containing compound are immobilised, they may be immobilised on the same electrode or on separate electrodes.

Operation of an $H_2S$ Sensor

An electrochemical reaction of a redox active compound may couple to a reaction of an analyte and act as a catalyst for its reaction. This analyte can be determined by means of an amperometric measurement to measure any increase in the electric current which flows when the analyte is present: the magnitude of the increase in current provides a measure of the concentration of the analyte.

The redox reaction of a ferrocenophane-containing compound can couple to the oxidation of hydrogen sulfide to sulfur, so that the concentration of hydrogen sulfide can be determined from the increase in current compared to the current which flows in the absence of hydrogen sulfide. The reactions can be written as $Fcp \rightarrow Fcp^{\cdot +} + e^-$ $Fcp^{\cdot +} + HS^- \leftrightarrows Fcp + S + H^+$ A ferrocenophane-containing compound can also be used in the determination of other analytes, analogously to the use of ferrocene carboxylate for analytes such as ascorbic acid, briefly mentioned in Electroanalysis vol 18 pp 1658-1663 (2006) and in references cited by that paper.

An electrochemical sensor which includes a ferrocenophane-containing compound could be incorporated into a wide variety of tools and equipment. Possibilities include use in tools which are located permanently downhole, use in tools which are conveyed downhole, for instance at the head of coiled tubing or by drillpipe or on a wireline, use in underground, undersea or surface pipeline equipment to monitor liquid flowing in the pipeline, and use in a wide variety of process plant at the Earth's surface, including use in water treatment.

Figure 5:
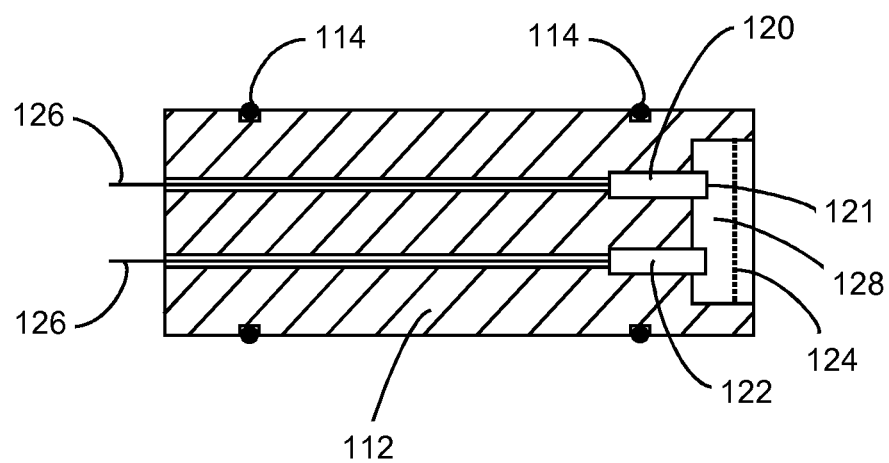
FIG. 5 is a diagrammatic cross section of a sensor unit.

FIG. 5 illustrates in cross section an embodiment of sensor unit. It has a main body 112 which is cylindrical. This body is intended to be accommodated inside a cylindrical cavity in a wellbore tool or other structure and is encircled by two sealing rings 114 to provide a seal between the body 112 and the cavity accommodating it. The body 112 supports an electrode 120, and a counter electrode 122. Electrical connections to the electrodes are indicated at 126. The electrodes 120 and 122 are in contact with an electrolyte retained by a membrane 124 within a cavity 128 at the end 129 of the body 112. This membrane 124 separates the electrolyte from the external fluid under test, but is permeable to the species such as hydrogen ($H^+$) ions and bisulfide ($HS^-$) whose concentration is to be measured. The electrolyte retained by membrane 124 may be aqueous or may be acetonitrile. Dissolved in this electrolyte is a compound containing a ferrocenophane group such as the sulfonate salt made in Example 3 above.

If the sensor of FIG. 5 is used to measure $H_2S$ diffusing through the membrane 124, the ferrocenophane compound becomes coupled to the oxidation to sulfur, as explained above. If the sensor is used to measure hydrogen ions diffusing through the membrane 124, the electrolyte retained by the membrane may contain anthraquinone as a pH sensitive redox active compound while the ferrocenophane-containing compound acts as a pH insensitive reference.

Figure 6:
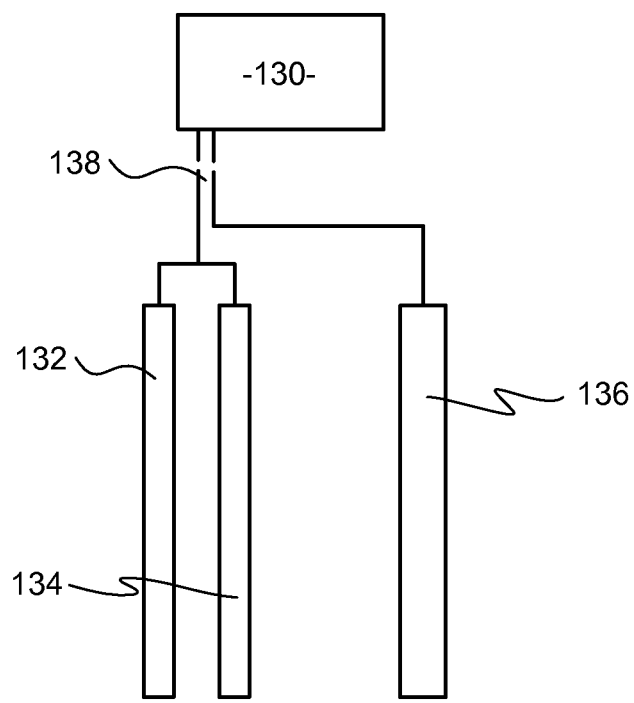
FIG. 6 is a diagrammatic illustration of the parts of an electrochemical sensor.

FIG. 6 diagrammatically illustrates apparatus which may be used in pH measurement. A working electrode 132 has carbon particles derivatized with a pH-sensitive redox active compound immobilized on its surface. A reference electrode 134 has carbon particles derivatized with a ferrocenophane-containing compound immobilized on its surface. There is also counter electrode 136. All the electrodes are connected by cable or other wiring indicated at 138 to a potentiostat 130 or other control unit which provides electric power and measurement. The various electrodes are immersed in or otherwise exposed to fluid whose pH is to be measured.

A control unit such as 130 may comprise a power supply, voltage supply, potentiostat and/or the like for applying an electrical potential to the working electrode 132 and a detector, such as a voltmeter, a potentiometer, ammeter, resistometer or a circuit for measuring voltage and/or current and converting to a digital output, for measuring a potential between the working electrode 132 and the counter electrode 136 and/or potential between the working electrode 132 and the reference electrode 134 and for measuring a current flowing between the working electrode 132 and the counter electrode 136. The control unit 130 may in particular be a potentiostat serving to sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 130 may include signal processing electronics.

Figure 7:
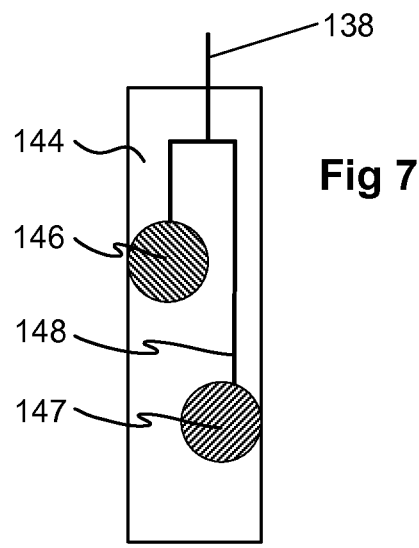
FIG. 7 shows another electrode construction.

FIG. 7 shows a possible variation. A conductive paste containing carbon derivatized with a pH sensitive redox compound is printed on one area 146 of an insulating substrate 144 to provide an electrode 132. A second conductive paste containing carbon derivatized with a pH insensitive ferrocenophane-containing compound is printed on an area 147 as a reference electrode and both areas 146 and 147 are connected together and connected to a cable 138 leading to a control unit by conductive tracks 148 on the substrate 144. The electrodes 146, 147 may be screen printed onto the substrate 144 using stencil designs to delineate the areas of the electrode.

Figure 8:
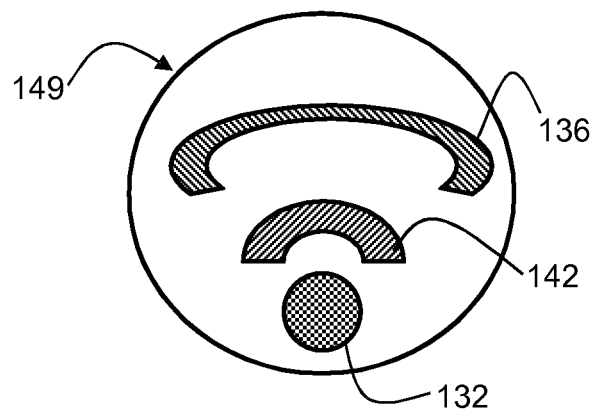
FIG. 8 illustrates the geometrical surface layout of the surface of a sensor.

FIG. 8 shows a possible geometric configuration or layout for the surface 149 of a sensor which is exposed to the fluid to be tested, which may, merely by way of example be a wellbore fluid. The surface includes a disk shaped working electrode 132, a second electrode 142 which is carbon with a ferrocenophane compound chemically immobilized on it and a counter electrode 136.

Figure 9:
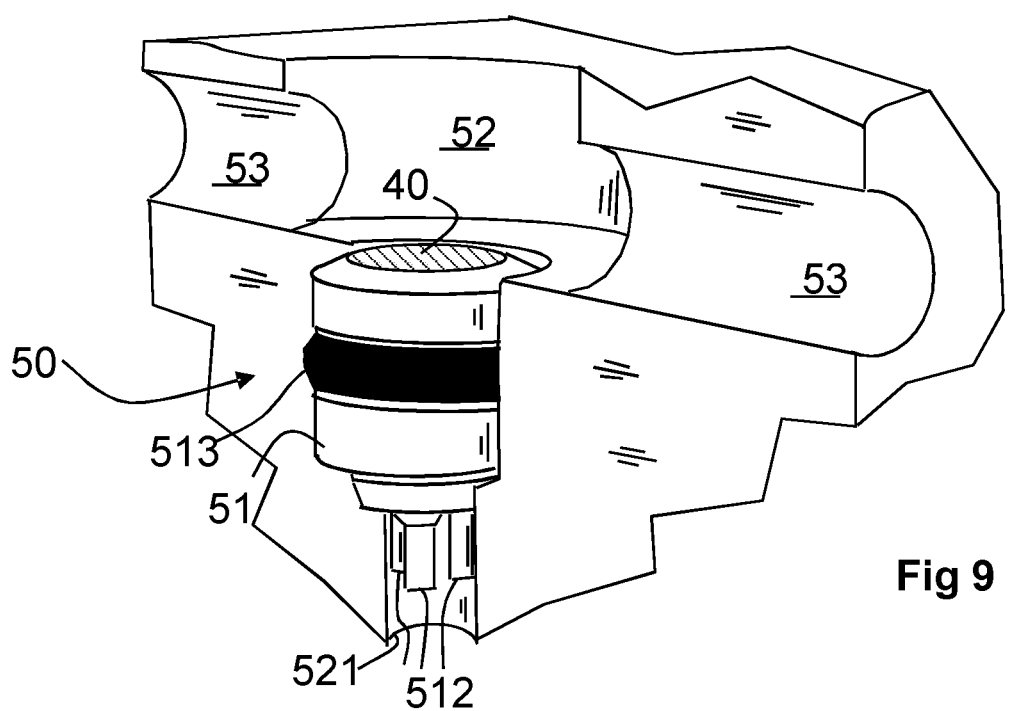
FIG. 9 is a perspective view, partially cut-away, of an electrochemical sensor incorporating the surface of FIG. 8.

A schematic of a microsensor 50 incorporating such a surface is shown in FIG. 9. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the fluid to be tested that passes under operation conditions through the sample channel 53.

Figure 10:
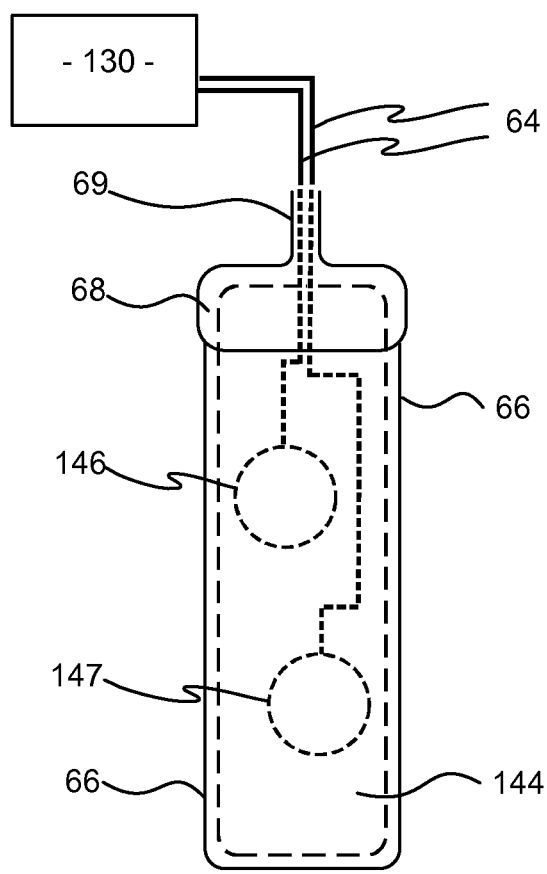
FIG. 10 illustrates a working electrode covered at least in part by a polymer layer.

FIG. 10 shows an insulating substrate 144 carrying a screen printed working electrode on an area 146 and a screen printed reference electrode on an area 147. These are not connected together but are connected by separate conductors within a cable 64 to a potentiostat 130 which may be a handheld device. After deposition of electrode materials onto the substrate 144, the substrate and deposited materials were coated with a permeable polymer layer indicated by reference 66. Methods to deposit the polymer in a generally uniform layer include spin coating, dip coating and application using solvent evaporation. One end of the coated substrate has an impermeable covering 68 which merges with the sheath 69 of the cable 64. A polymer coating 66 which is permeable to water and other small molecules may prevent derivatized carbon from becoming detached from the electrodes, but still allow for interactions with an analyte. For example a permeable polymer coating may comprise a polysulfone polymer or a polystyrene polymer.

Figure 11:
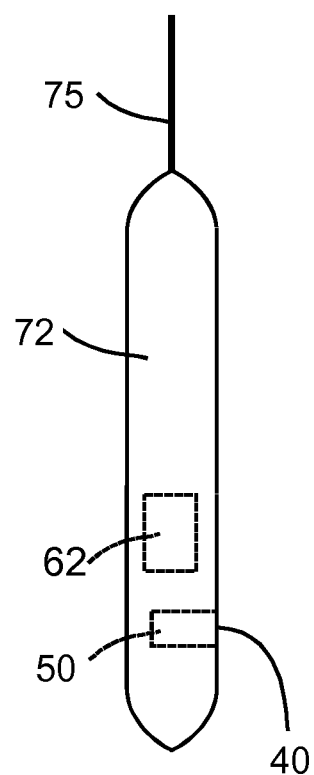
FIG. 11 is a diagrammatic illustration of a cable-suspended tool for testing water.

One application of an electrochemical sensor may lie in the monitoring of underground bodies of water for the purposes of resource management. Using monitoring wells drilled into the aquifers, one or more sensors may be deployed on a cable from the surface. The sensor(s) may be in place for a relatively short duration (as part of a logging operation) or a longer term (as part of a monitoring application). FIG. 11 illustrates a tool for investigating subterranean water. This tool has a cylindrical enclosure 72 which is suspended from a cable 75. A sensor unit such as that of FIG. 5 is accommodated within the enclosure 72 so that its membrane 124 exposed to the subterranean water. Alternatively a sensor unit such as the sensor 50 shown in FIG. 9 is accommodated within the enclosure 72 with its surface 149 exposed to the subterranean water. The tool also encloses a unit 130 for supplying voltage to the electrodes 120 and 122 or 132, 142 and 136, and measuring the current which flows and transmitting the results to the surface.

The sensor may be a pH sensor. Suspending such a device on a cable within producing wells may provide information on produced water quality. Also, the pH sensor may be deployed in injection wells, e.g. when water is injected into an aquifer for later retrieval, where pH may be used to monitor the quality of the water being injected or retrieved.

Figure 12:
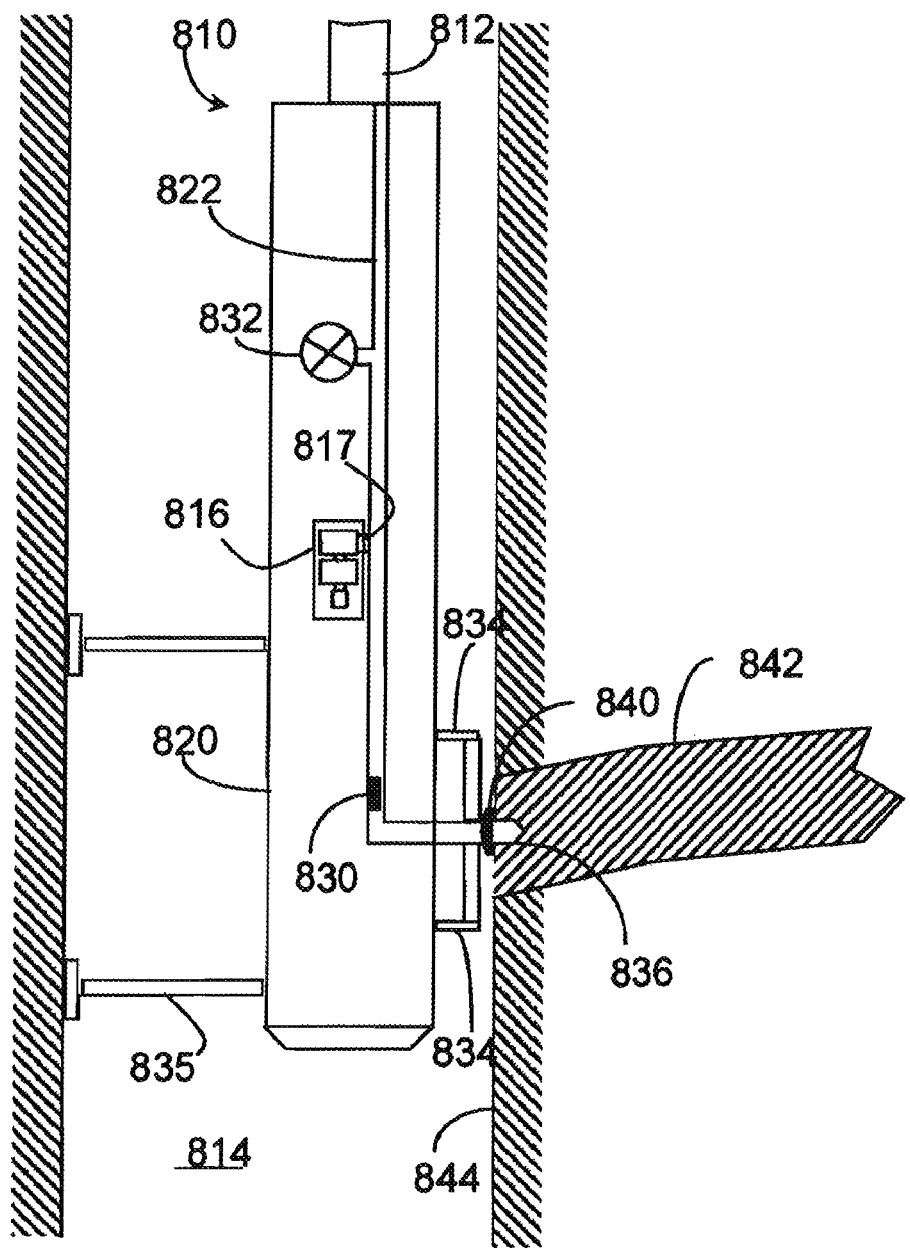
FIG. 12 illustrates an example of an electrochemical sensor, as part of a wireline formation testing apparatus in a wellbore.

FIG. 12 shows a formation testing apparatus 810 held on a wireline 812 within a wellbore 814. The apparatus 810 is a well-known modular dynamic tester (MDT, Trade Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of an electrochemical analyzing sensor 816 substantially similar to sensor 50 of FIG. 9 The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The O-ring 840 at the base of the sample probe 836 forms a seal between the side of the wellbore 844 and the formation 842 into which the probe 836 is inserted and prevents the sample probe 836 from acquiring fluid directly from the borehole 814. Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical sensor 816 can then measure the pH or concentration of another analyte such as hydrogen sulfide in the formation effluent.

While the preceding uses of an electrochemical sensor are in the hydrocarbon and water industries, embodiments of electrochemical sensor incorporating derivatized carbon may be used for detecting an analyte in a whole host of industries, including food processing, pharmaceutical, medical, water management and treatment, and biochemical industries, as well as research laboratories. A polymer coating may prevent escape of derivatized carbon particles from an electrode into the fluid around it, but still allow for interactions between an analyte and one or more redox active compounds on the electrode.

The invention claimed is:

1. An electrochemical sensor for an analyte, the electrochemical sensor comprising:
   a reference electrode comprising a first redox active compound and a working electrode comprising a second redox active compound, wherein the first redox active compound and the second redox active compound differ in sensitivity to a concentration of the analyte;
   an aqueous electrolyte; and
   a control unit including one or more components that apply an electrical potential to the working electrode and measure one or more of voltage or current;
   wherein the first redox active compound:
      comprises a ferrocenophane with at least one bridging group comprising a chain of atoms covalently attached to and connecting two cyclopentadiene rings associated with a single iron atom, wherein the chain of atoms in the bridging group is a continuous chain of at least three carbon atoms between the two cyclopentadiene rings of the ferrocenophane, and wherein a first cyclopentadiene ring of the two cyclopentadiene rings is coupled to a benzyl group via an alkoxy;
      is thermally stable at an elevated temperature of about 120° C.; and
      is dissolved in the aqueous electrolyte.

2. The electrochemical sensor of claim 1, wherein the second redox active compound comprises a reversible reduction or oxidation at a voltage sensitive to a concentration of hydrogen ions.

3. The electrochemical sensor of claim 2, wherein the second redox active compound is an aromatic quinone or a hydroxylamino-substituted aromatic moiety.

4. The electrochemical sensor of claim 1, wherein the first redox active compound comprises at least one ionic group.

5. The electrochemical sensor of claim 1, wherein the control unit includes:
   voltammetric means to apply a variable voltage to the working electrode of the electrochemical sensor and to measure current while the voltage is systematically varied.

6. The electrochemical sensor of claim 1, wherein the electrochemical sensor is a hydrogen sulfide sensor or a thiols sensor.

7. The electrochemical sensor of claim 1, wherein the second redox active compound is attached to the first redox active compound.

8. The electrochemical sensor of claim 1, wherein the aqueous electrolyte is retained by a membrane and the reference electrode and the analyte are in contact with the aqueous electrolyte, a molar quantity of the analyte being at least 100 times greater than a molar quantity of the first redox active compound.

9. The electrochemical sensor of claim 1, wherein the benzyl group is coupled to graphite.

10. The electrochemical sensor of claim 1, wherein the benzyl group comprises a carbene group, an aldehyde group, a hydroxyl group, or an alkyl halide.

11. The electrochemical sensor of claim 1, wherein the ferrocenophane is 4-(6-[3]ferrocenophanylhexoxy)benzaldehyde, 4-(6-[3]ferrocenophanylhexoxy)benzyl alcohol, or 4-(6-[3]ferrocenophanylhexoxy)benzyl bromide.

12. The electrochemical sensor of claim 1, wherein the alkoxy chain is a hexoxy group.

13. A downhole tool for measuring characteristic parameters of wellbore fluids, comprising the electrochemical sensor of claim 1.

14. The downhole tool of claim 13, which is configured to be suspended in a hydrocarbon wellbore.

15. The downhole tool of claim 13, which is configured to be suspended in a well for monitoring groundwater.

16. A method of determining a concentration of an analyte in a liquid, comprising:
   contacting the liquid with the electrochemical sensor of claim 1;
   applying varying potential between the working electrode and the reference electrode; and
   measuring current as voltage is varied.

17. The method of claim 16, wherein the analyte is hydrogen ions and the ferrocenophane is used as a reference which is insensitive to analyte concentration.

18. The method of claim 16, wherein the analyte is hydrogen sulfide or thiols.

\* \* \* \* \*